US007613572B2

(12) United States Patent
Ben-Gal et al.

(10) Patent No.: US 7,613,572 B2
(45) Date of Patent: Nov. 3, 2009

(54) STOCHASTIC MODELING OF SPATIAL DISTRIBUTED SEQUENCES

(75) Inventors: Irad Ben-Gal, Ramat HaSharon (IL); Armin Shmilovici, Tel Aviv (IL); Gail Morag, Herzlia (IL); Gonen Zinger, Hadera (IL)

(73) Assignee: Context-Based 4 Casting (C-B4) Ltd., Herzlia (IL)

(*) Notice: Subject to any disclaimer, the term of this patent is extended or adjusted under 35 U.S.C. 154(b) by 444 days.

(21) Appl. No.: 10/468,101

(22) PCT Filed: Feb. 20, 2002

(86) PCT No.: PCT/IL02/00131

§ 371 (c)(1),
(2), (4) Date: Aug. 15, 2003

(87) PCT Pub. No.: WO02/067075

PCT Pub. Date: Aug. 29, 2002

(65) Prior Publication Data

US 2004/0068332 A1    Apr. 8, 2004

Related U.S. Application Data

(60) Provisional application No. 60/269,344, filed on Feb. 20, 2001.

(51) Int. Cl.
*G06F 19/00* (2006.01)
*G06F 15/00* (2006.01)

(52) U.S. Cl. .......................................... 702/19; 700/1

(58) Field of Classification Search .................. None
See application file for complete search history.

(56) References Cited

U.S. PATENT DOCUMENTS

| | | | |
|---|---|---|---|
| 4,719,571 | A | 1/1988 | Rissanen et al. |
| 5,640,159 | A | 6/1997 | Furlan et al. |
| 5,763,159 | A | 6/1998 | Simmmonds et al. |
| 5,903,676 | A | 5/1999 | Wu et al. |
| 5,907,637 | A | 5/1999 | Murashita et al. |
| 5,986,591 | A | 11/1999 | Willems et al. |
| 6,542,640 | B1 | 4/2003 | Morihara et al. |
| 2003/0061015 | A1 | 3/2003 | Ben-Gal et al. |

OTHER PUBLICATIONS

Ben-Gal et al, "Design of Control and Monitoring Rules for State Dependent Processes", *Int. J. Manufacturing Science & Prod.*, Invited paper, 3, Nos. 2-4, 2000, pp. 85-93.
Ben-Gal et al, Context-Based Statistical Process Control: A Monitoring Procedure for State-Dependent Processes:, *Technometrics*, 45(4):293-311, 2003.
Ben-Gal et al, "Statistical Process Control Via Context Modelling of Finite-State Processes: An Application to Production Monitoring", *IIE Transactions*, 36:401-415, 2004.
Shmilovici et al, "Context Dependent ARMA Modeling", *21st IEEE Convention*, Tel-Aviv, 2000, pp. 249-252.
Morag et al, "Design of Control Charts Based on Context Universal Model", *Industrial Engineering and Management Conference*, Israel, 2000, pp. 200-204.
Ben-Gal et al, "Statistical Control of Production Processes via Monitoring of Buffer Levels", *The 9th International Conference on Productivity & Quality Research*, Jerusalem, Israel, 2000, pp. 340-347.
Shmilovici et al, "Statistical Process Control for a Context Dependent Process Model", *The Annual Euro Operations Research Conference*, Budapest, Hungary, Jul. 16-19, 2000.
Ben-Gal et al, "An Information Theoretic Approach for Adaptive Monitoring of Processes", ASI2000, *The Annual Conference of ICIMS—NOE and IIMB*, Bordeaux, France, 2000, p. 2.6.3-2.6.6.
Ben-Gal et al, "A Methodology for Integrating Engineering Process Control and Statistical Process Control", *Proc. of The 16th International Conference on Production Research*, Prague, Czech Republic. Jul. 29-Aug. 3, 2001.
Ben-Gal et al. "Design of Control and Monitoring Rules for State Dependent Processes", The International Journal for Manufacturing Science & Production, Invited Invited Paper, 3(2-4): 85-93, 2000.
Ben-Gal et al. "Context-Based Statistical Process Control: A Monitoring Procedure for State-Dependent Processes", Technometrics, 45(4): 293-311, 2003.
Shmilovici et al. "Context Dependent ARMA Modeling", 21st IEEE Convention, Tel-Aviv: 249-252, 2000.
Morag et al. "Design of Control Charts Based on Context Universal Model", Industrial Engineering and Management Conference, Israel: 200-204, 2000.
Ben-Gal et al. "Statistical Control of Production Processes Via Monitoring of Buffer Levels", Proceedings of the 9th International Conference on Productivity & Quality Research, p. 340-347, 2000.
Shmilovici et al. "Statistical Process Control for A Context Dependent Process Model", Proceedings of the Annual EURO Operations Research Conference, Budapest, Hungary, 2 P., 2000.
Ben-Gal et al. "A Methodology for Integrating Engineering Process Control and Statistical Process Control", Proceedings of the 16th International Conference on Production Research, Prague, CZ, 2 P., 2001.

(Continued)

*Primary Examiner*—John S Brusca

(57) ABSTRACT

Apparatus for building a stochastic model of a spatially related data sequence, the data sequence comprising symbols selected from a finite symbol set, the apparatus comprising: an input for receiving said data sequence, a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence. The tree may then be used to carry out a comparison with a new data sequence to determine a statistical distance between the old and the new data sequence.

45 Claims, 20 Drawing Sheets

OTHER PUBLICATIONS

Singer et al. "Implementation of the Context Tree for Statistical Process Control", Department of Industrial Engineeering Tel Aviv University, 2000.

Rissanen "A Universal Data Compression System", IEEE Transactions on Information Theory, 29(5): 656-664, 1983.

Weinberger et al. "A Universal Finite Memory Source", IEEE Transactions on Information Theory, 41(3): 643-652, 1995.

Qian "Relative Entropy: Free Energy Associated With Equilibrium Fluctuations and Non-Equilibrium Deviations", Physical Review E., 63: 042103/1-042103/4, 2001. http://arxiv.org/abs/math-ph/007010.

Weinberger et al. "Sequential Model Estimation for Universal Coding and the Predictive Stochastic Complexity of Finite-State Sources", Proceedings of the IEEE International Symposium on Information Theory, p. 52, 1993.

ICIMS-NOE "Advanced Summer Institute 2000: The Annual Conference of the ICIMS-NOE (E.P.23447) Jointly With the Workshop on Integration in Manufacturing & Beyond IIMB 2000. Life Cycle Approaches to Production Systems: Management, Control, Supervision", Bordeaux France, Sep. 18-20, 2000. Http"//www.lar.ee.upatras.gr/icims/asi/asi2000/asi2000.htm.

Official Action Dated May 7, 2007 From the US Patent and Trademark Office Re.: U.S. Appl. No. 10/076,620.

Official Action Dated Dec. 27, 2005 From the US Patent and Trademark Office Re.: U.S. Appl. No. 10/076,620.

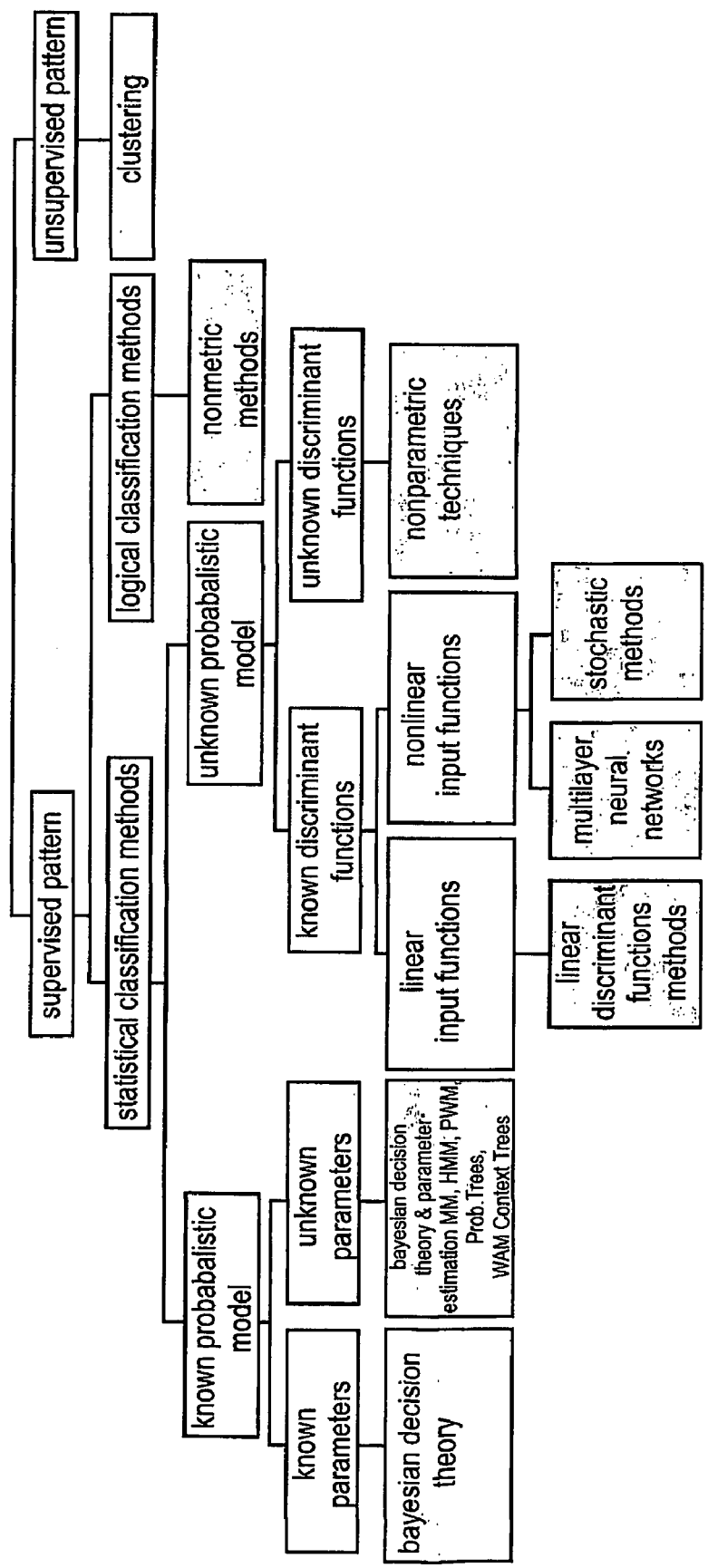
FIG. 1A  Pattern recognition categories

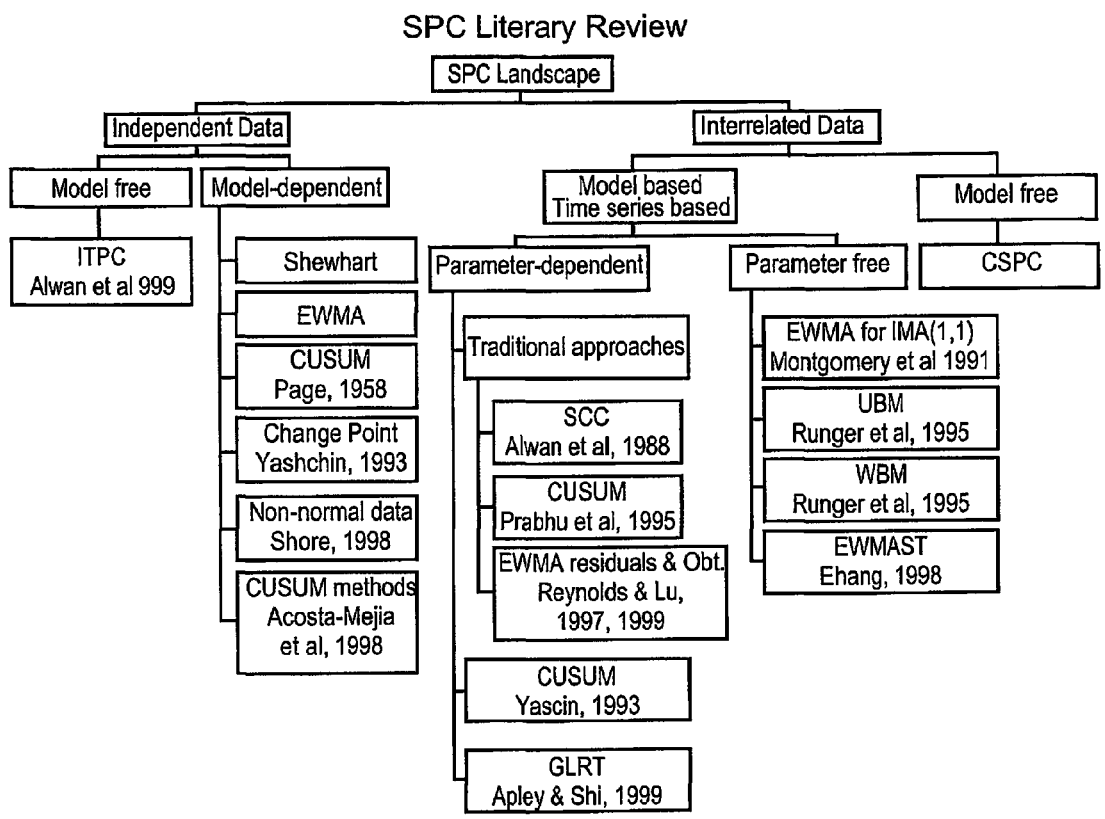
FIG. 1D   SPC Characterization methods

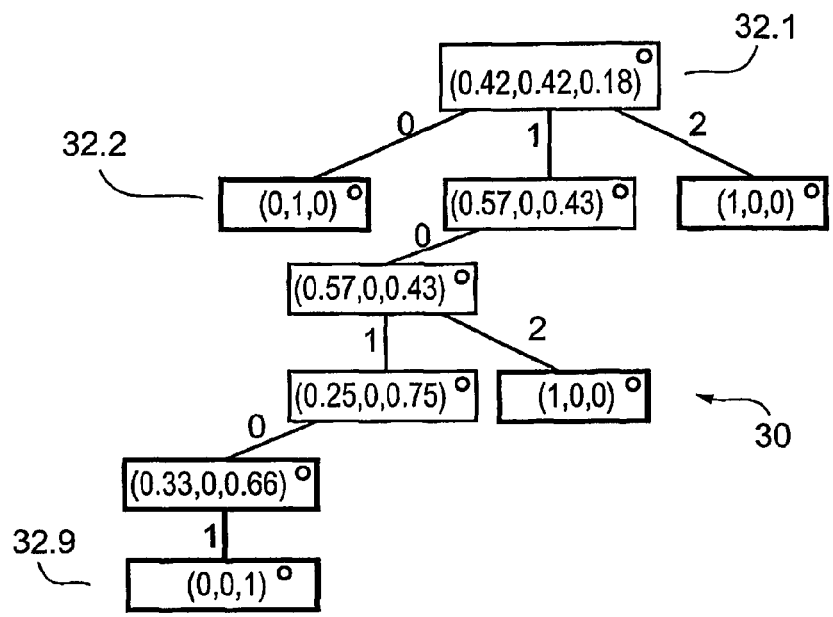
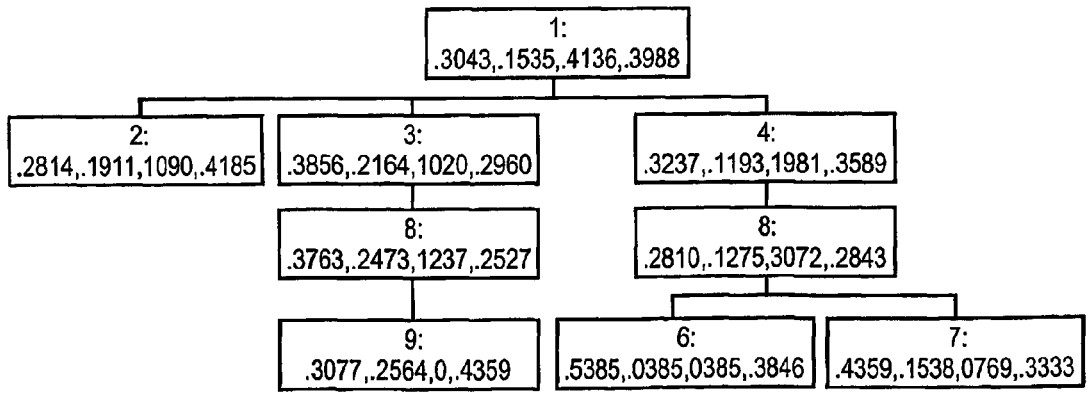
Fig. 3b
A context tree generated by one replicate of 238 E. Coli promotes

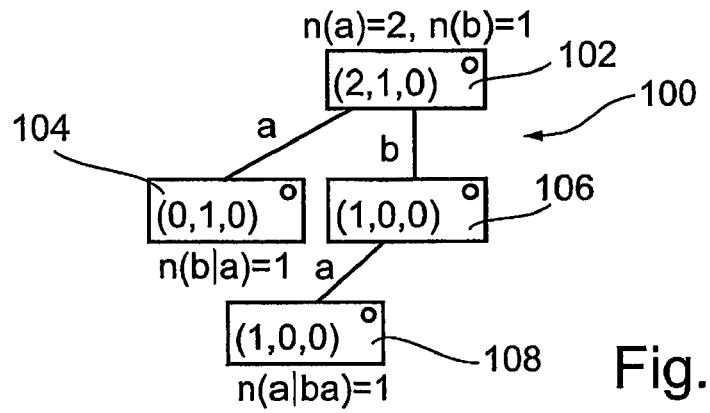
The counter context tree constructed from $x_3$=a,b,a
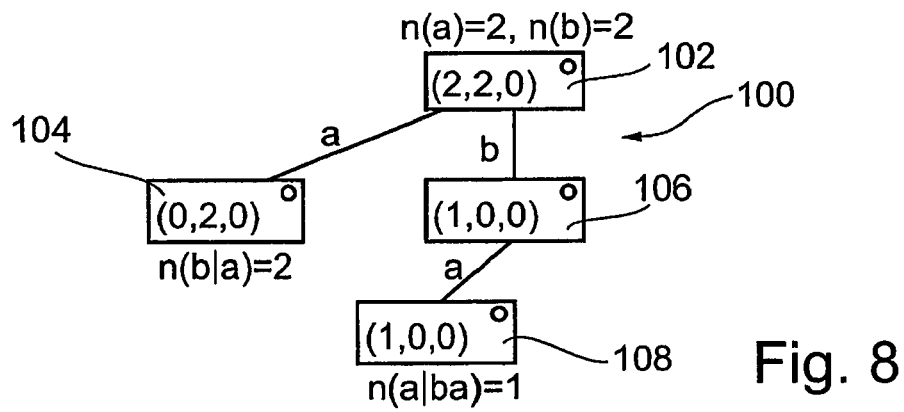
The counter context tree constructed from $x^4$=a,b,a,b following step 1.1
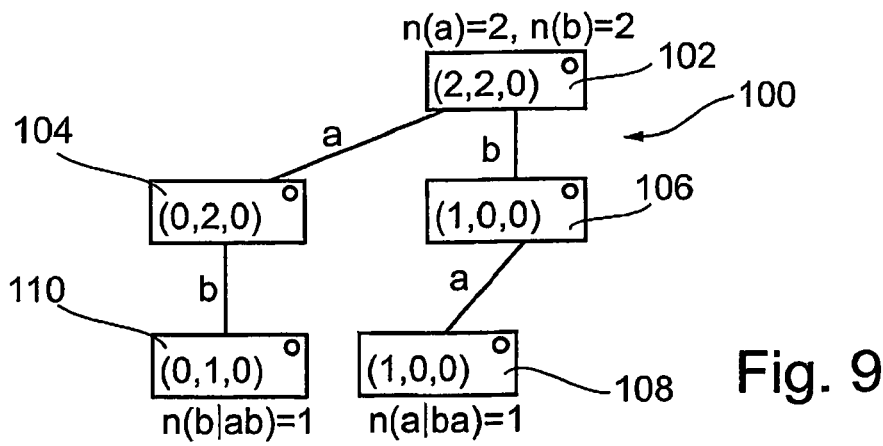
The counter context tree constructed from $x^4$=a,b,a,b; partial application of step 1.2

The pruned counter context-tree of the string (a,b,a,b,c,a,b,a,b,c,a,b,a,b,a,b,c) replicated 8 times The context tree containing vectors of conditional probabilities P(x/s) as obtained from the counter context-tree in figure A4. Optimal contexts are represented by the bolded frame

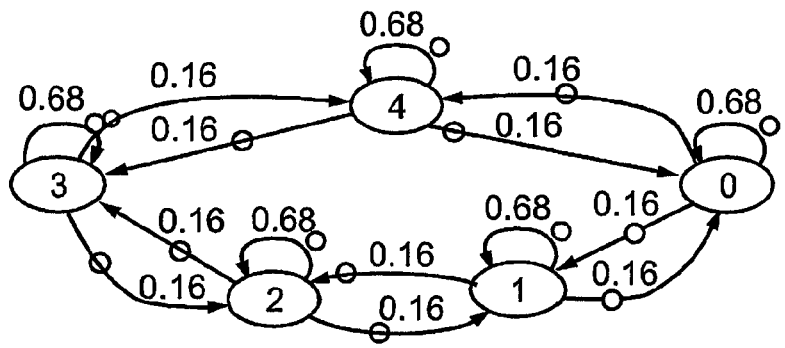
Fig. 12 State transition diagram
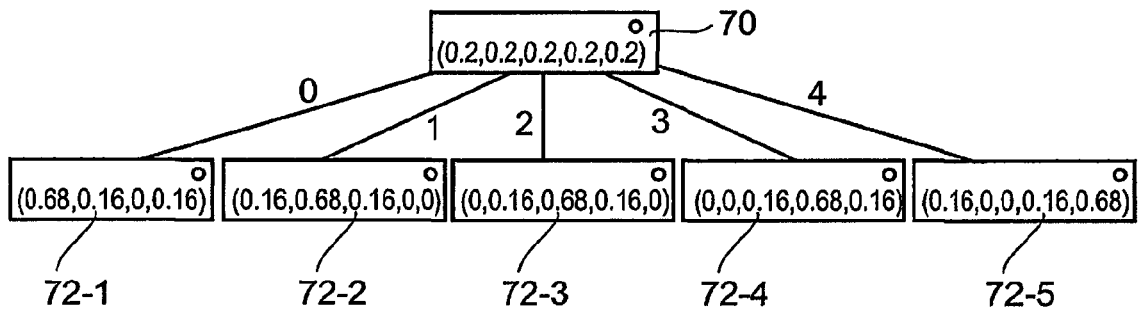
Fig. 13 The analytically derived singled-level context-tree
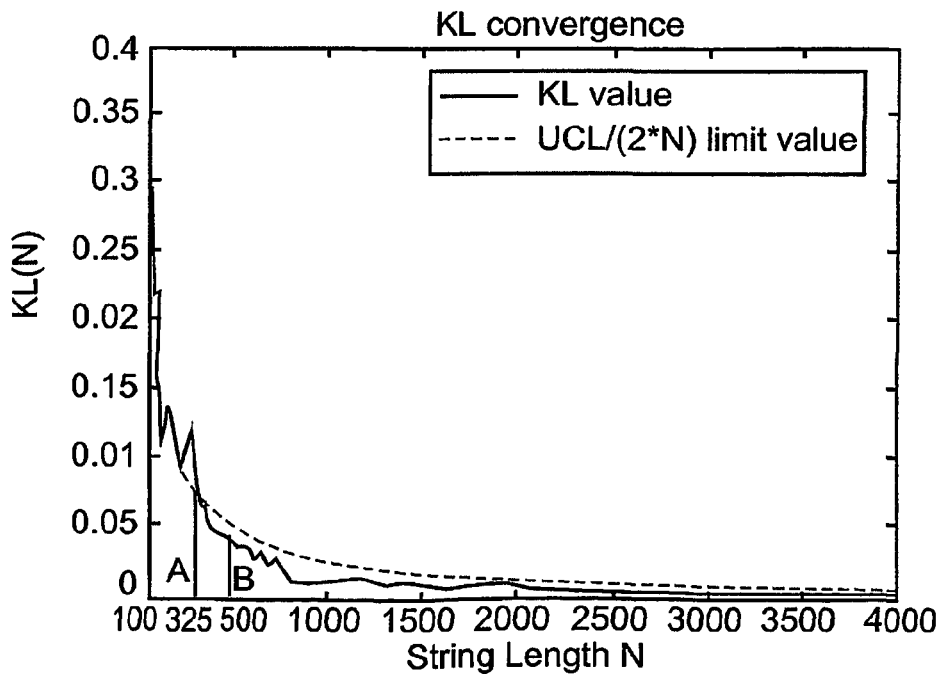
Fig. 14 KL value in relation to input string length N

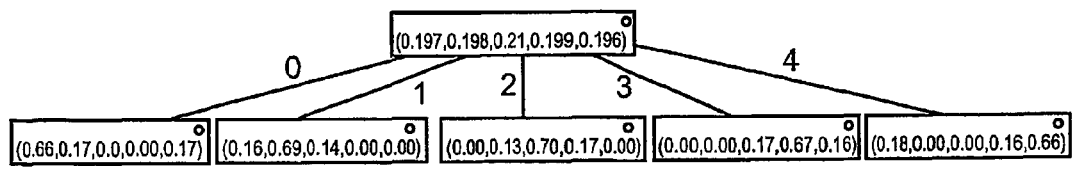
Fig. 15 Estimated reference context-tree resulted from the implementation of context algorithm to $N=1000$
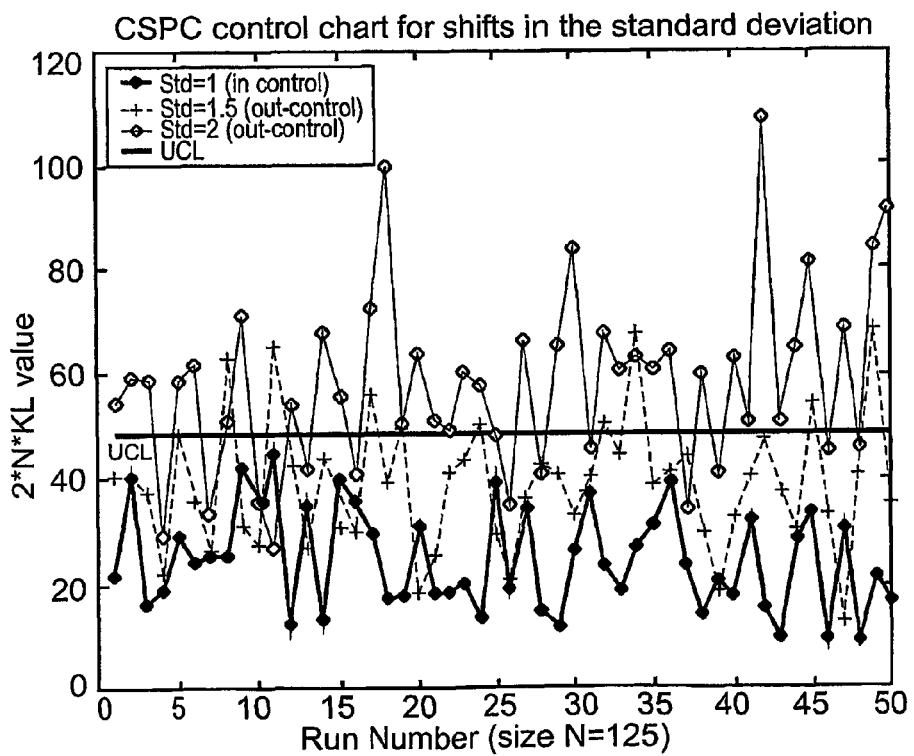
Fig. 16
Shifts in the process underlying normal standard deviation
-$\lambda$=1,1.5,2 (number of runs for each process properties is equal to 50)

Shift in the process underlying normal standard deviation
-λ=0.5 (number of runs equal to 50)

Operating characteristics curve

The SCC control chart for "in-control" data

Shewhart SPC $\overline{X}$ chart-"in-control" data (solid line) and "out-of-control" data (thin line)

Shewhart SPC S chart-"in-control" data (solid line) and "out-of-control" data (dashed line)

Shewhart SPC $\overline{X}$ chart for N=125 sample size -"in-control" data (solid line) and "out-of-control" data (dashed line)

Shewhart SPC S chart for N=125 sample -"in-control" data (solid line) and "out-of-control" data (dashed line)

STOCHASTIC MODELING OF SPATIAL DISTRIBUTED SEQUENCES

RELATIONSHIP TO EXISTING APPLICATIONS

The present application claims priority from Provisional U.S. Patent Application No. 60/269,344, filed on 20 Feb. 2001, the contents of which are hereby incorporated by reference.

RELATED PATENT APPLICATION

This application is a National Phase Application of PCT/IL02/00131 International Filing Date 20 Feb. 2002, International Publication No. WO 02/067075, International Publication Date Aug. 29, 2002.

FIELD OF THE INVENTION

The present invention relates to stochastic modeling of sequences and more particularly but not exclusively to modeling of data sequences representing spatial distributions using stochastic techniques, and again but not exclusively for using the resultant models for analysis of the sequence.

BACKGROUND OF THE INVENTION

Data sequences often contain redundancy, context dependency and state dependency. Often the relationships within the data are complex, non-linear and unknown, and the application of existing control and processing algorithms to such data sequences does not generally lead to useful results.

Statistical Process Control (SPC) essentially began with the Shewhart chart and since then extensive research has been performed to adapt the chart to various industrial settings. Early SPC methods were based on two critical assumptions:

i) there exists a priory knowledge of the underlying distribution (often, observations are assumed to be normally distributed); and ii) the observations are independent and identically distributed (i.i.d.).

In practice, the above assumptions are frequently violated in many industrial processes.

Current SPC methods can be categorized into groups using two different criterea as follows:

1) methods for independent data where observations are not interrelated versus methods for dependent data;
2) methods that are model-specific, requiring a priori assumptions on the process characteristics and its underlying distribution, and methods that are model-generic. The latter methods try to estimate the underlying model with minimum a priori assumptions.

FIG. 1 is a chart of relationships between different SPC methods and includes the following:

Information Theoretic Process Control (ITPC) is an independent-data based and model-generic SPC method. It utilizes information theory principles, such as maximum entropy, subject to constraints derived from dynamics of the process. It provides a theoretical justification for the traditional Gaussian assumption and suggests a unified control chart, as opposed to traditional SPC that require separate charts for each moment.

Traditional SPC methods, such as Shewhart, Cumulative Sum (CUSUM) and Exponential Weighted Moving Average (EWMA) are for independent data and are model-specific. It is important to note that these traditional SPC methods are extensively implemented in industry. The independence assumptions on which they rely are frequently violated in practice, especially since automated testing devices increase the sampling frequency and introduce autocorrelation into the data. Moreover, implementation of feedback control devices at the shop floor level tends to create structured dynamics in certain system variables. Applying traditional SPC to such interrelated processes increases the frequency of false alarms and shortens the 'in-control' average run length (ARL) in comparison to uncorrelated observations. As shown later in this section, these methods can be modified to control autocorrelated data.

The majority of model-specific methods for dependent data are time-series based. The underlying principle of such model dependent methods is as follows: assuming a time series model family can best capture the autocorrelation process, it is possible to use that model to filter the data; and; then apply traditional SPC schemes to the stream of residuals. In particular, the ARIMA (Auto Regressive Integrated Moving Average) family of models is widely applied for the estimation and filtering of process autocorrelation. Under certain assumptions, the residuals of the ARIMA model are independent and approximately normally distributed, to which traditional SPC can be applied. Furthermore, it is commonly conceived that ARIMA models, mostly the simple ones such as AR(1), can effectively describe a wide variety of industry processes.

Model-specific methods for autocorrelated data can be further partitioned into parameter-dependent methods that require explicit estimation of the model parameters, and to parameter-free methods, where the model parameters are only implicitly derived, if at all.

Several parameter-dependent methods have been proposed over the years for autocorrelated data, and proposed the Special Cause Chart (SCC) in which the Shewhart method is applied to the stream of residuals. They showed that the SCC has major advantages over Shewhart with respect to mean shifts. The SCC deficiency lies in the need to explicitly estimate all the ARIMA parameters. Moreover, the method performs poorly for a large positive autocorrelation, since the mean shift tends to stabilize rather quickly to a steady state value, and the shift is poorly manifested on the residuals.

Some approaches implemented traditional SPC for autocorrelated data using CUSUM methods, extended the method by using the EWMA method with a small difference. Their model had a random error added to the ARIMA model. The drawback of these models is in the exigency of an explicit parameter estimation and estimation of their process-dependence features. It was demonstrated that for certain autocorrelated processes, the use of traditional SPC yields an improved performance in comparison to ARIMA-based methods.

The Generalized Likelihood Ratio Test—GLRT—method takes advantage of residuals transient dynamics in the ARIMA model, when a mean shift is introduced. The generalized likelihood ratio may be applied to the filtered residuals. The method may be compared to the Shewhart, CUSUM and EWMA methods for autocorrelated data, inferring that the choice of the adequate time-series based SPC method depends strongly on characteristics of the specific process being controlled. Moreover, in and it is emphasized in conclusion that modeling errors of ARIMA parameters have strong impacts on the performance (e.g., the ARL) of parameter-dependent SPC methods for autocorrelated data. If the process can be accurately defined by an ARIMA time series, the parameter independent SPC methods are superior in comparison to non-parametric methods since they allow efficient statistical analysis. If such a definition is not possible, then the effort of estimating the time series parameters becomes impractical. Such a conclusion, amongst other reasons, triggered the development of parameter-free methods to avoid the impractical estimation of time-series parameters.

A parameter-free model was proposed as an approximation procedure based on EWMA. They suggested using the EWMA statistic as a one step ahead prediction value for the IMA(1,1) model. Their underlying assumption was that even if the process is better described by another member of the ARIMA family, the IMA( 1,1) model is a good enough approximation. An approach however, compared several SPC methods and showed that Montgomery's approximation performed poorly. He proposed employing the EWMA statistic for stationary processes, but adjusted the process variance according to the autocorrelation effects.

An approach discussed the weighted batch mean (WBM) and the unified batch mean (UBM) methods. The WBM method assigns weights for the observations mean and defines the batch size so that the autocorrelation among batches reduces to zero. In the UBM method the batch size is defined (with unified weights) so that the autocorrelation remains under a certain level.

Runger and Willemain demonstrated that weights estimated from the ARIMA model do not guarantee a performance improvement and that it is beneficial to apply the simpler UBM method. In general, parameter-free methods do not require explicit ARIMA modeling, however, they are all based on the implicit assumption that the time-series model is adequate to describe the process. While this can be true in some industrial environments, such an approach cannot capture more complex and non-linear process dynamics that depend on the state in which the system operates, for example processes that are described by Hidden Markov Models (HMM).

The Problem of Pattern Classification

In general, the goal of pattern recognition, is to classify objects of interest into one of a number of categories or classes. The objects of interest are called patterns, and they may be printed as letters or characters, biological cells, electronic wave-forms or signals, "states" of a system or any number of other things that one may desire to classify. If there exists some set of labeled patterns, namely their class are known, then one has a problem in supervised pattern recognition. The basic procedure followed in design of a supervised pattern recognition system involves a portion of a set of labeled patterns being extracted and used to derive a classification algorithm. These patterns are called the training set. The remaining patterns are then used to test the classification algorithm; these patterns are collectively referred to as the test set. Since the correct classes of the individual patterns in the test set are also known, the performance of the algorithm can be evaluated. In supervised pattern recognition problems, the results are preferably evaluated by a "teacher" or "supervisor" whose output dictates suitable modifications to the algorithm—hence the term supervised pattern recognition. Once a desired level of performance is achieved (which is measured in terms of a misclassification rate), the algorithm can be used on initially unlabeled patterns. At this point, the feedback loop involving the teacher is formally broken. Nonetheless it is usually advisable to have some spot-checking of results. Such checks can be accommodated either by providing an alternative classification algorithm or a human observer if possible. In some situations it may be feasible to wait a certain length of time until the correct classification is known. If the classes of all of the available patterns are unknown, and perhaps even the number of these classes is unknown, then one has a problem in unsupervised pattern recognition or clustering. In clustering problems, one attempts to find classes of patterns with similar properties where sometimes even these properties may be undefined. The unsupervised pattern recognition or clustering problem is a much more difficult one than the supervised pattern recognition problem. Nevertheless, useful algorithms have been developed in this area and success depends to a large extent on the ability to learn the structure of pattern measurement data in high-dimensional spaces. The present disclosure focuses on a supervised pattern recognition scheme.

The Patterns Recognition Approach:

In the typical pattern recognition approach, observations first undergo feature transformation and then classification in order to arrive at an output decisions. An observation vector x is first transformed, by the feature transformation, into another vector y whose components are called features. The features are intended to be fewer in number than the observations but should collectively contain most of the information needed for classification of the patterns. By reducing the observations to a smaller number of features, one hopes to design a decision rule that is more reliable. The feature vector y can be represented in a feature space Y similar to the way that observation vectors are represented in the observation space. The dimension of the feature space, however, is usually much lower than the dimension of the observation space. Procedures that analyze data in an attempt to define appropriate features are called feature extraction procedures. The feature vector y is passed to a classifier whose purpose is to make a decision about the pattern. The classifier essentially induces a partitioning of the feature space into a number of disjoint regions. If the feature vector corresponding to a pattern falls into region Ri, the pattern is assigned to class Wi.

In general, the symbol x is used herein to represent observation vectors and y is used to represent feature vectors.

There are several ways to perform patterns recognitions. We classify the pattern recognition methods into different classes, as shown in the tree depicted in attached FIG. 1A. We will detail those branches in the tree that are related to the present disclosure.

The first classification is between supervised pattern recognition vs. unsupervised pattern recognition:

In supervised pattern recognition, the types and the number of the existing classes are known. In addition, the classes in the training set are tagged.

By contrast, in unsupervised pattern recognition, the classes of all of the available patterns are unknown, and in some cases even the number of these classes is unknown. Consequently, in such situation the classes in the training set are not tagged and the problem becomes a clustering problem.

The present disclosure concerns problems of supervised pattern recognition, since, as will be explained below in the description of the specific embodiments, the construction algorithm may make use of the different tagged classes in the training set to generate a different context-tree model for each class, for example, in the promoter recognition problem there are two tagged classes: "promoters" and "non-promoters". We thus continue to detail the supervised pattern recognition branch.

The second classification distinguishes between statistical and logical methods.

Logical Methods are usually used when the classification problems involves nominal data, for instance description, that are discrete and without any natural notion of similarity or even ordering. The decision tree is an example of a logical method. This branch is irrelevant to the present disclosure.

Statistical Methods use statistical tools and they are based on feature vectors of real-valued and discrete-valued numbers. There can be a natural measure of distance between theses vectors. In this category, which is relevant to the present disclosure, we make another distinction between Unknown probabilistic models and Known probabilistic models.

In unknown probabilistic models, the underlying probabilistic model is unknown. In many cases researchers make use of discriminant function to address these types of problems. Since we assume that a general context-tree model can well represent the different classes (although the parameters of the tree are unknown and need to be estimated from the training set), we do not consider this branch of methods.

Known probabilistic models—the distribution function or a general probabilistic model, such as transition probabilistic tree, is assumed known. We assume that a general context-tree model can well represent the different classes. In this category, which is relevant to the present disclosure, we distinguish between the following two types of models:

Known parameters—models based on known parameters. This is often the easiest albeit the more rare problem. In this case, researches typically use Bayesian decision theory to classify the unknown object.

Unknown parameters—in these cases, researches often estimate the parameters by known methods such as the maximum likelihood estimation (where parameters are assumed to be fixed), Bayesian estimation (where parameters are assumed to be random variable), and Gibbs sampling. To this branch of methods the present disclosure belongs. This branch includes some other state-dependent models such as: and Markov models, Hidden Markov Models, Neural nets etc. Note that once the parameters of the model are estimated then conventional methods of classification can be used such as those based on Bayesian decision theory.

Giving the above classification, note that Markov models are the closest methods to the suggested disclosure presented here. In the following, we briefly sketch the Markov models.

Markov Models

Markov models are based on a finite memory assumption, i.e., that each symbol depends only on its k formers, where k is fixed. The simplest model is first-order Markov model, which assume that each symbol at time t depends only on the symbol at time t-1: $P(x_i=W(i)|x_1=W(1), x_2=W(2), \ldots, x_{i-1}=W(i-1))=P(x_i=W(i)|x_{i-1}=W(i-1))$, where state i at time t is denoted by $W_i(t)$.

In order to calculate the probability that the model generates a particular sequence, the successive probabilities should simply be multiplied.

Markov models of higher order simply extend the size of the memory. The suggested methods of the present disclosure can be viewed as a varying-order Markov model, since the order of the memory doesn't have to be fixed as explained latter.

In general, Markov Models assume that the states are accessible. In many cases, however, the perceiver does not have access to the states. Consequently, Markov Model should be augmented to Hidden Markov Model, which is a Markov model with invisible states. Hidden Markov models have a number of parameter whose values are set so as to best explain training patterns for the known category.

An alternative model to the Markovian is the context-tree that was suggested by for data compression purposes and modified later in. The tree presentation of a finite-memory source is advantageous since states are defined as contexts—graphically represented by branches in the context-tree with variable length—and hence, requires less estimation efforts than those required for a Markov presentation. The context-tree is an irreducible set of conditional probabilities of output symbols given their contexts. The tree is conveniently estimated by context algorithm. The algorithm generates an asymptotically minimal tree fitting the data. The attributes of the context-tree along with the ease of its estimation make it suitable for a model-generic classifier, as explain later.

Patterns Classification in Biology

Applications of Pattern Recognition in Biology

The following is a summary of Prof. Shamir's lecture notes available at Internet web site mathdottaudotacdotil/~rshamir/ and from Higgins D. G. and Taylor W. R. (2000), "Multiple sequence alignment", Methods Mol Biol., 143, 1-18. The sequences of the family members in Biology are often compared in order to find properties that are shared by all members and understand how these could explain certain biological properties. Discovering patterns in biology is widespread, and has two main applications: i). Classification: the patterns are to be used for discriminating between family members and non-members; and ii) finding patterns that describe biologically important features.

In the following we briefly describe some of the main applications of patterns recognition in Biology. Note that the present embodiments are applicable to all these problems.

Coding Sequences in Prokaryotic Gene Structure

There are more than 3 billions bases of human, albeit eukaryotic, DNA sequences and complete DNA sequences for dozens of species available in GenBank. Not all the sequences are coding, namely are a template for a protein. In the human genome only 3%-5% of the sequences are coding sequences, and the approximate proportion applies also to prokaryotic sequences. Due to the size of the database, there is a need to find a way for automatic finding of coding sequences. The algorithm should look for long sequences of codons, without any stop codon. It should scan the DNA sequence, looking for long ORF's (open reading frame) in all three reading frames (the first codon can start from the first, second or the third basic). After detecting a stop codon, the algorithm scans backward, searching for a start codon.

It should be noticed that the coding sequence has no fixed length, a fact that creates difficulties on the pattern recognition algorithm. A typical prokaryote sequence is shown in FIG. 1B.

Exons in Eukaryotic Sequences

The gene structure and the gene expression mechanism in eukaryotes are far more complicated than in prokaryotes. In typical eukaryotes, the region of the DNA coding for a protein is usually not continuous. This region is composed of alternating stretches of exons and introns. During transcription, both exons and introns are transcribed onto the RNA, in their linear order. Thereafter, a process called splicing takes place, in which the intron sequences are excised and discarded from the RNA sequence. The remaining RNA segments, the ones corresponding to the exons, are ligated to form the mature RNA strand. A typical multi-exon gene has the following structure: It starts with the promoter region, which is followed by a transcribed but non-coding region called 5' untranslated region (5' UTR). Then follows the initial exon which contains the start codon. Following the initial exon, there is an alternating series of introns and internal exons, followed by the terminating exon, which contains the stop codon. It is followed by another non-coding region called the 3' UTR. Ending the eukaryotic gene, there is a polyadenylation (polyA) signal: the nucleotide Adenine repeating several times. The exon-intron boundaries (i.e., the splice sites) are signaled by specific short (2 bp long) sequences. The 5'(3') end of an intron (exon) is called the donor site, and the 3'(5') end of an intron (exon) is called the acceptor site. FIG. 1C represents a typical eukaryote sequence structure.

Exon length does not have a geometric distribution. The length seems to have a functional role on the splicing itself. Typically, exons that are too short (under 50 bp) leave no room for the spliceosomes (enzymes that perform the splicing)

to operate and exons that are too long (above 300 bp) are being difficult to locate. Thus another model for exon length is required.

An algorithm for this kind of recognition, should notice the differences between the exons and the introns, and the connections between them. It also should take into consideration the different length distribution: an average internal exon is about 150 bp long, while introns of the order of 1 Kbp length are not uncommon.

Promoters

A promoter is a region of DNA to which RNA polymerase binds before initiating the transcription of DNA into RNA:

Not all open reading frames are transcribed into genes. The transcription depends on regulatory regions that control the transcription rate. In the transcription process, an RNA polymerase binds tightly to the promoter. The promoter is an 'anchor' point, it pinpoints where RNA transcription should begin. At the stop signal the polymerase releases the RNA and detaches itself from the DNA. We further distinguish between two cases i) Prokaryotic Promoters:

The promoter contains two remote pairs of six basics. In one example of our invention, which is described latter, we identify *E. coly* promoters. In *E. coly* one can find the following consensus sequence around RNA transcription start point:

nnnTTGACAnnnnnnnnnnnnnnnnnnnTATAATnnnnnnNnnn.

N is the transcription start point. TTGACA appears 35 bases before N, and TATAAT (also known as TATA box or Pribnow box) appear 12 bases before N. We have here 2 anchor points for the polymerase. These sequences are short but the frequency of their occurrence is high.

Since the consensus sequence mentioned above doesn't appear in each promoter, an algorithm should be developed in order to recognize a pattern that will suit all the promoters.

ii) Eukaryotic Promoters:

Much less is known about eukaryote promoters; each of the three RNA polymerases has a different promoter.

RNA polymerase I recognizes a single promoter for the precursor of rRNA.

RNA polymerase II, that transcribes all genes coding for polypeptides, recognizes many thousands of promoters. Most have the Goldberg-Hogness or TATA box that is centred around position −25 and has the consensus sequence 5'-TATAAAA-3'. Several promoters have a CAAT box around −90 with the consensus sequence 5'-GGCCAATCT-3'. There is increasing evidence that all promoters for genes for "housekeeping" proteins contain multiple copies of a GC-rich element that includes the sequence 5'-GGGCGG-3'. Transcription by polymerase II is also affected by more distant elements known as enhancers.

The promoter for RNA polymerase III is located within the gene either as a single sequence, as in the 5s RNA gene, or as two blocks, as in all tRNA genes.

Splice Sites

The Splice Sites Structures are:

```
5' splice sites:
MAG|GTRAGT where M is A or C and R is A or G

3' splice sites:
CAG|GT
```

An algorithm might predict the splice sites that distinguish between the exons and the introns.

Terminators

At the end of the coding sequences a signal exists (the terminator) which means "stop making RNA here". It is composed of a sequence which is rich in the bases G and C and which can form a hairpin loop. This structure is more strongly hydrogen bonded (G-C base pairs are held together by three hydrogen bonds) causing the RNA polymerase to slow down.

Poly A

Polyadenylic acid sequence of varying length found at the 3' end of most eukaryotic mRNAs. The poly-A tail is added post-transcriptionally to the primary transcript as part of the nuclear processing of RNA yielding hnRNAs with 60-200 adenylate residues in the tail. In the cytoplasm the poly-A tail on mRNAs is gradually reduced in length. The function of the poly-A tail is not clear.

It is useful to find the pattern of the Polyadenylic acid.

Proteins

Proteins are long chains of Amino Acids (AA). There are 20 types of AA that serve as building blocks for proteins. Each AA has a specific chemical structure. The length of a protein chain can range from 50 to 3000 AA (200 on the average). One of the interesting properties of proteins is the unique folding. The AA composition of a protein will usually uniquely determine (on specific environment conditions) the 3D structure of the protein (e.g., two proteins with the same AA sequence will have the same 3D structure in natural conditions). Researches of 3D structure of proteins have shown that when a folded protein is artificially stretched to a chain, it folds back to it's original 3D structure. Proteins are known to have many important functions in the cell, such as enzymatic activity, storage and transport of material, signal transduction, antibodies and more. All proteins whose structure is known are stored in the Protein DataBank (PDB), which contains more than 10,000 proteins.

A protein has multiple levels of structure:

Primary structure—Chain of Amino Acids (1 dimensional).

Secondary structure—Chains of structural elements, most important of which are $\alpha$-helices and $\beta$-sheets.

Tertiary and Quaternary structure—3D structure, of a single AA chain or several chains, respectively.

The pattern recognition of proteins is done in these three levels: primary structure (20 symbols), secondary structure and 3D structure.

Classification Concepts in Biology

Pattern-Based Classification Approaches

An approach proposed a general three-step approach for discovering patterns from protein and DNA sequences:

i) Choose a solution space (a set of patterns that the method should discover).

ii) Define a fitness function reflecting how well a pattern fits the input sequence.

iii) Develop an algorithm, which gets a set of input sequences, and returns the patterns with the highest fitness According to one approach, there are two main groups of sequence patterns: Deterministic patterns (Regular expression type patterns) and Probabilistic patterns. Next, both types of patterns are described.

Deterministic Patterns

In deterministic pattern methods, a sequence either matches or does not match the pattern.

A very simple type of patterns is a substring pattern—a sequence matches a substring pattern if it contains the substring. When matching a sequence against a substring pattern there are two kinds of matching: exact and approximate.

When using approximate matching, a sequence matches the pattern if it contains a substring approximately equal to the pattern. "Approximately equal" means that only some of the characters are the same.

In the approximate matching, a distance is defined between a pattern and a substring, and an upper limit on the distance (a threshold) is set.

Typical ways to measure the distance between two strings are:
i) Hamming distance—counting the number of character changes needed to transform one into the other (number of mismatches). The measure is relevant only for two strings of the same size.
ii) Gaps based methods. In these methods in order to match the two strings, it's allowed to insert or delete characters in addition to their substitutions (namely, gaps are allowed).

```
For          ACCDDECA versus ACDDECA
example:

Without      ACCDDECA
gaps:
             II I

ACDDECA (3 matches)

With         ACCDDECA
gaps:
             I IIIIII

A_CDDECA (7 matches, one gap of 1 length)
```

In the above methods, the distance is a function of the number of mismatches, the number of gaps and their length.

Alternatively, there are methods that define a score between a pattern and a sub string and set a lower limit on the score to be allowed.

The advantages of the deterministic patterns are that they are very simple, mathematically pure and easy to interpret. Its disadvantage is that often, there is more one pattern that matches all the family members.

Probabilistic Patterns

In these patterns for each position in the pattern, a score is assigned to each of the symbols (e.g., four basics in D.N.A, or twenty amino acids in proteins). Additionally, penalties (or probabilities) to insertions or deletions in each pattern position are assigned. These can also be seen as generalization of substring patterns. These methods assign a score (probability) to a match to a sequence.

This category contains: Profiles (Position Specific Scoring Matrixes), HMM (Hidden Markov Models) and Probabilistic Trees. All these methods are relative methods to the suggested algorithm as further detailed below.

In the probabilistic patterns the probabilities are often calculated from:
i) the distribution of the symbols (e.g., amino acids or basics) in the columns of the probability matrices.
ii) some external information from substitution matrices.
iii) Dirichlet mixtures.

The invention presented here derives the probability measures of symbols based on their type, position and context. However, the set of probabilities to be used for classification is determined by the algorithm in a different manner than the above-mentioned methods.

The advantages of probabilistic patterns are that they can be used when it is not possible to define one single regular expression type pattern, which matches all family sequences. They can assign different scores and different gap penalties to each symbol in different pattern position. Their disadvantages are that they contain many more parameters to be estimated, and in order to estimate their values, a large number of family members is needed. In addition, noisy examples can enter the learning process, and therefore unmatched sequences will be recognized as matched.

Pattern and Sequence Driven Algorithms

An approach identified two main algorithmic approaches: Pattern Driven (PD) methods and Sequence Driven (SD) methods.

Pattern driven methods: In the simplest form, PD methods enumerate all patterns in the solution space calculating each pattern's fitness so that the best ones can be output. There are more sophisticated methods that contain mechanisms for avoiding looking at all patterns in the solution space.

Sequence driven methods: In these methods different pairs of sequences are compared in order to find similarities as patterns. These methods are very similar to the sequence alignment methods. Examples for sequence driven methods are:
i) A further approach developed a method that first computes the similarity between all pairs of input sequences. The most similar pair is input to a local pair-wise alignment method that is based on dynamic programming. This algorithm outputs a pattern common to the two sequences. The two sequences aligned are replaced by their common pattern and the procedure is repeated until there remains only one pattern matching all the input sequences.
ii) The Pratt programs gets as input a set of sequences and finds patterns matching at least a minimum number of the sequences that is defined by the user. The user can also input constrains on the patterns (the solution space). Pratt uses a two steps search (initial pattern search and pattern refinement) for finding conserved patterns (patterns that match at least the minimum number of the sequences) from the chosen solution space having maximum fitness.

The invention presented here is related to sequence driven methods, since patterns are not enumerated. Instead, the training sequence are used to construct the tree model which represent probabilistically a set of patterns.

Fitness Functions

Fitness functions usually reflect how well a pattern fits the input sequence. Some fitness function are designed according to the following principles:
i) According to an approach, information content of a pattern is a measure of the information gained about an unknown sequence when one is told that the sequence matches the pattern.
ii) An approach described the minimum description length (MDL) principle, which assigns a score to a pattern that depends on the pattern's information content and on how many sequences it matches. The user can select parameters in order to slant the optimum towards strong patterns matching few sequences or towards weaker patterns matching many sequences.
iii) PPV (Positive Predictive Value)—It is usually used by the Pratt program when the aim is to find patterns to be used for classification.

The invention presented here makes use of the tree model to derive a fitness function to each sequence.

Training the Model

In methods of supervised pattern-recognition (and particularly in those related to biology pattern recognition), a portion of the set of labeled patterns is extracted and used to derive a classification algorithm. These patterns comprise the training set.

The remaining patterns are then used to test the classification algorithm; these patterns are referred to as the test set. Since the correct classes of the individual patterns in the test set are also known, the performance of the algorithm can be evaluated. There is a tradeoff between the classification of the training samples and the performance of the algorithm on new objects. Perfect classification of the training samples can be achieved, but in this case new objects that were not part of the training set usually are not well recognized. This situation is known as overfitting, and it should be avoided. Thus, It is very important to determine how to adjust the complexity of the model: it shouldn't be so simple that it cannot explain the differences between the categories, yet, not so complex as to give poor classification on novel patterns. There are several ways to evaluate the algorithm. Two of them are:

iv) Parametric Models: The generalization error rate is computed from the assumed parametric model. A test set is not needed in these models.

v) Simple Cross-Validation: The set of labeled samples D are split into two parts, as mentioned above. One part is used as the traditional training set. The other part is the validation set, which is used to estimate the error rate. The classifier is trained until one reaches a minimum of this error.

vi) General Cross-Validation: in more detail.general cross validation methods, the performance is based on multiple, independently formed validation sets. For example, in the m-fold cross validation, the training set is randomly divided into m disjoint sets of equal size. The classifier is trained m times, each time with a different set held out as a validation set. The estimated performance is the mean of these m errors. In the Anti-cross validation the adjustment of parameters is halted when the validation error is the first local maximum.

Conventional Performance Measure

When a pattern is to be used for classification, it should ideally match all family members and no other sequences. Most often, however, the pattern fails to match some member sequences (called false negatives), and it may match some sequences outside the family (called false positives). The fewer false negatives, the more sensitive the pattern is said to be, and the fewer false positives, the more specific it is. Ideally, a pattern should have zero false positives and negatives.

An estimate of the number of matches in a sequence database can be found by multiplying the probability that one random sequence matches the pattern by the number of sequences in the database. In order to calculate the probability, it is often assumed that random sequences are generated using a specific probabilistic model. considered all the patterns in the PROSITE database and obtained a clear correlation between the expected number of false positives and the actual number, i.e., the number of unrelated sequences in the SWISS-PROT database matching the pattern.

Denoting the number of true positives (sequences in the family matching the pattern) by TP and the number of false negatives by FN, the sensitivity of a pattern can be defined as, Sensitivity=$TP/(TP+FN)$.

The sensitivity measures of how big a proportion of the family sequences are 'picked up by' (matched by) the pattern. Similarly, the specificity of the pattern can be defined as, Specificity=$TN/(TN+FP)$, (where TN and FP are, respectively, the number of true negatives and the number of false positives) which measures of how big a proportion of the sequences outside the family are not matched by the pattern. Yet, another useful measure is the positive predictive value (PPV), which determines how big a proportion of the sequences matching the pattern are actually in the family, i.e.,

PPV=$TP/(TP+FP)$.

The value range for all the above measures is from zero to one—one being the best possible. When evaluating patterns to be used for classification, one needs to use more than one of the measures. This can be illustrated by two degenerate cases, (1) the empty pattern matching any member, and (2) a pattern matching one single member in the family. Pattern (1) has perfect sensitivity, but very bad specificity and PPV, while pattern (2) has perfect specificity and PPV, but bad sensitivity. In practice, one often needs to make a trade-off between sensitivity and specificity when choosing which pattern to use for a family. One way to evaluate a probabilistic pattern's ability to discriminate between family members and other sequences is to find a cut-off on the score that gives the same number of false positives and false negatives. An approach evaluated alternative ways of finding weight matrices from local ungapped alignments using this approach. Another approach is to achieve maximum TP given very high TN. This approach relies on the assumption that the proportion of the negatives in the population is very high.

Used Models for Pattern Classification in Biology

Some general probabilistic methods are often used to recognize a number of families in biology. Some of the most common methods sharing the same idea are Profiles (Position Specific Scoring), PWM (Positional Weight Matrix) and WMM (Weight Matrix Model). This methods are often referred as Non-Homogeneous models, which mean that the distribution of the symbols is different between one position in the pattern to the other.

Researchers initially suggested the profiles Matrixes. Profile is a scoring matrix giving a position specific scoring and specific gap penalties for each symbol (amino acids or basics). The matrix, known as the PWM, is a table of statistics, $f_{b,i}$, of the frequencies of the symbol b in position i of the known sequences (e.g., promoter or coding). This model assumes that positions are independent. GENSCAN uses different signal models to model different functional units. One of the models is WMM in which every position has its own specific independent distribution. It is used for modeling polyadenylation signals, translation initiation signal, translation termination signal and promoters.

Another model is the weighted array model (WAM). The WAM model is a generalization of the WMM model that allows dependencies between adjacent positions. The WAM model is used for the recognition of the splice sites. Correct recognition of these sites greatly enhances ability to predict correct exon boundaries. This modeling of splice sites gave GENESCAN a substantial improvement in performance. This model can be seen as the extension of HMM, since each position has its own HMM network.

As was mentioned before, a hidden Markov models (HMM) is a Markov chain in which the states are not directly observable. Instead, the output of the current state is observable. The output symbol for each state is randomly chosen from a finite output alphabet according to some probability distribution.

Another approach uses three interpolated Markov Chains of different order, which are trained on coding, non-coding and promoter sequences.

A Generalized Hidden Markov Model (GHMM) generalizes the HMM as follows: in a GHMM, the output of a state may not be a single symbol. Instead, the output may be a string of finite length. For a particular current state, the length of the output string as well as the output string itself might be randomly chosen according to some probability distribution. The probability distribution need not be the same for all states. For example, one state might use a weight matrix model for generating the output string, while another might use a HMM. Formally a GHMM is described by a set of four parameters:

i) A finite set Q of states.
ii) Initial state probability distribution $\Pi_q$.
iii) Transition probabilities $T_{i,j}$ for $i,j \in Q$.
iv) Length distributions f of the states ($f_q$ is the length distribution for state q).
v) Probabilistic models for each of the states, according to which, output strings are generated upon visiting a state.

The probabilistic model for gene structure, is based on a GHMM.

Another model is the probabilistic tree model. In the probabilistic tree model, similarly to the Markov models (MM), the probability of each symbol depends on its k predecessors. The deferent between MM and probabilistic trees is that in MM k is fixed, and in the probabilistic trees k is changeable. In practice, k is selected to attain the shortest contexts for which the conditional probability of a symbol given the context is practically equal to the conditional probability of that symbol given the whole data. For example, researchers used probabilistic suffix trees in order to model protein families. The construction of the suffix tree, the parameterization and growth is different than the tree model presented here (for example, the construction of suffix tree requires multi-passes as oppose to a single pass in the context tree, moreover, "partial leafs" that might have a vital importance for classification are ignored in suffix trees). Another researcher used a similar tree model for text clustering. The suggested invention is a relative to these methods yet differs from them as indicated below.

In the following, we indicate a list/survey of models that were investigated for several classification applications.

Proteins

Researchers reviewed methods for prediction of functional sites, tRNA and protein coding genes, and classified the protein coding algorithms to five groups:

i) Codon usage—using the frequencies of the 64 codons.
ii) Encoded amino acid sequence.
iii) Base compositional bias between codon positions—These algorithms consider the different between the three-codon positions. See, for example,
iv) Imperfect periodicity in base occurrences.
v) Other global patterns.

Promoters

Researchers made a review of the identification and analysis of eukaryotic promoters:

Discovering Motifs

Researchers divided the discovering motifs methods into two main categories—Alignment methods and Enumerative or exhaustive methods.

Alignment methods aim to identify unknown signals by a significant local multiple alignment of all sequences. Alignment approaches deliver a model of the motifs (such as a weight matrix) built from the alignment. They require different statistics depending on how often a pattern may be present in the sequences.

There are Direct multiple alignment methods, such the consensus algorithm, which aligns sequences one by one and optimize the information content of the weight matrix constructed from the alignment.

There are also statistical approach methods. They consider the start positions of the motifs in the sequences to be unknown and perform a local optimization to determine which positions deliver the most conserved motif. Examples of these methods are: Gibbs sampling and expectation maximization in the MEME system.

In the other hand, the enumerative or exhaustive methods aim to examine all oligomers of a certain length and report those that occur far more often than expected from the overall promoter sequence composition. These methods give a list of over-represented oligomers, possibly already grouped to form consensus sequences. They have to use an elaborate background model to judge the importance of frequent patterns. They also need to have the size of the motif specified in advance.

The Set of Input Data

The methods are often applied on a set of promoters that were first grouped together using gene expression measurements. A new way to look at the data is to cluster genes based on both expression levels and common motifs. An alternative approach is to identify elements by analyzing promoters of the same gene from approximately ten different related species.

Promoters Recognition Algorithms:

Researchers divided these algorithms into two main groups based on different search principles:

i) Search by signal algorithms—making predictions based on the detection of core promoter elements such as TATA box or the initiator and/or transcription factor binding sites outside the core.
ii) Search by content algorithms—identifying regulatory regions based on the sequence composition of promoter and nonpromoter examples.

There are also methods that combine both ideas—looking for signals and for regions of specific composition. Other methods and ideas for finding the promoters are:

i) Providing an accurate prediction of the TSS (transcription start site). This idea is good only for small regions known to contain a promoter.
ii) Providing specific prediction of regulatory regions using a search by content approach. The method gives no information regarding whether the affected gene is on the leading or lagging strand, or where the TSS itself is located within the region.
iii) Constructing specific, rather than general, promoter models for groups of genes as muscle-active genes known by experiment-to contain specific combination of regulatory elements.

researchers presented a set of discriminant functions that can recognize promoters in the human genome. They explain the implementation of these functions into a decision tree that constitutes a new program called FirstEF. They obtained a TP=86% with FN=17%.

Other researchers provide a review for the eukaryotic promoter recognition methods:

Researchers used consensus sequences—giving the most preferred base at each position within a site. This approach loses much of the information and is of marginal utility.

PWM (positional weight matrix) assigns a weight to each possible nucleotide at each position of a putative binding site and gives as a site score the sum of these weights. PWM are more informative, and are used when enough information is available to build them.

A researcher developed an iterative algorithm for weight matrix refinement in order to find motifs in the promoters. This kind of model assumes nonhomogenous structure, which means that the symbols distribution is different between the positions in the pattern.

Interpulated HMM—In these techniques, the estimated probability of a sequence is the linear or other interpolation between all conditional probabilities with increasing context length. A researcher used three interpolated Markov Chains of different order, which are mainly used to recognize eukaryotic promoters. They compared promoters versus non promoters (coding sequences, intron sequences and both coding and non-coding sequences. The best accuracy was achieved in promoters versus CDS (T.N=95%, T.P.=88.9%, AC=91.95%)

Coding

Codon Frequencies in Coding Regions

An informative method to determine coding regions, takes advantage of the frequencies at which the various codons occur in coding regions. For example, the amino acids Leucine, Alanine and Tryptophan are coded by 6, 4 and 1 different codons respectively. In a translation of a uniformly random DNA sequence, these amino acids should occur in the ratio 6:4:1, but in a protein they occur at a different ratio—6.9:6.5:1. Therefore coding DNA is not random. Another example of the non-uniformity of coding DNA is the fact that A or T occurs in the $3^{rd}$ position of a codon in a rate over 90% (these statistics vary for different species).

Finding Long ORFs

Another way to distinguish coding regions from non-coding regions, is to examine the frequencies of stop codons. Assuming a uniform random distribution, a stop codon is expected to be observed every 64/3=21.33 codons (since there are 3 stop codons). Average proteins are much longer, being coded by about 1000 bp (base pairs). Each coding region has only one stop codon, which terminates the region. Therefore, one way to detect the coding regions, is to look for long sequences of codons, without any stop codon. The algorithm that uses the above idea scans the DNA sequence, looking for long ORFs in all three reading frames. Upon detecting a stop codon, the algorithm scans backward, searching for a start codon. This algorithm will fail to detect very short genes, as well as overlapping long ORFs on opposite strands. Moreover, there are a lot more ORFs than genes. For example, one can find 6500 ORFs in the DNA of the bacterium E. coli while there are only 4400 genes.

ORFs as Markov Chains

Assuming one finds all ORFs in a sequence, he can use codon frequencies to find which ORFs are coding and which are non coding open reading frames (NORFs). This is done by translating each ORF into a codon sequence and obtaining a 64-state Markov chain. One can use a state for each codon rather than a state for each amino acid, because codons are more informative than their translations (there might be a preference for a specific codon in gene expression over other codons that encode the same amino acid). The transition probabilities are the probabilities for each codon to follow any other codon in a coding region. Using this model, one can compute the probability that a given ORF is really a coding region.

Exons

Spliced Alignment

Given a genomic sequence and a set of candidate exons, the spliced alignment algorithm another researcher explores all possible exons assemblies and finds a chain of exons which best fits a related target protein. The set of candidate exons is constructed by considering all blocks between candidate acceptor and donor sites (i.e., between AG dinucleotide at the intron-exon boundary and GU dinucleotide at exon-intron boundary) and further filtration of this set. To avoid losing true exons, the filtration procedure is designed to be very gentle, and the resulting set of blocks may contain a large number of false exons. Instead of trying to identify the correct exons by further pursuit of statistical methods, The algorithm considers all possible chains of candidate exons and finds a chain with the maximum global similarity to the target protein.

Network Formulation

The spliced alignment problem can be formulated in network terms. The set of blocks is represented by a set of nodes βi. A node $v_i$ is connected to a node $v_j$ if $\beta_i < \beta_j$. The requested solution is the best alignment between the reference sequence (T) and a path in the network.

Further information is available from Ben-Gal I., Shmilovici A., Morag G., "Design of Control and Monitoring Rules for State Dependent Processes", *Journal of Manufacturing Science and Production*, 3, NOS. 2-4, 2000, pp. 85-93; also Ben-Gal I., Morag G., Shmilovici A., "Statistical Control of Production Processes via Context Monitoring of Buffer Levels", submitted (after revision); Ben-Gal I., Singer G., "Integrating Engineering Process Control and Statistical Process Control via Context Modeling", submitted, (after revision); Shmilovici A. Ben-Gal I., "Context Dependent ARMA Modeling", *Proc. of the 21st IEEE Convention*, Tel-Aviv, Israel, Apr. 11-12, 2000, pp. 249-252; Morag G., Ben-Gal I., "Design of Control Charts Based on Context Universal Model", *Proc. of the Industrial Engineering and Management Conference*, Beer-Sheva, May 3-4, 2000, pp. 200-204; Zinger G., Ben-Gal I., "An Information Theoretic Approach to Statistical Process Control of Autocorrelated Data", *Proc. of the Industrial Engineering and Management Conference*, Beer-Sheva, May 3-4, 2000, pp. 194-199 (In Hebrew); Ben-Gal I., Shmilovici A. Morag G., "Design of Control and Monitoring Rules for State Dependent Processes", *Proc. of the 2000 International CIRP Design Seminar*, Haifa, Israel, May 16-18, 2000, pp. 405-410; Ben-Gal I., Shmilovici A., Morag G., "Statistical Control of Production Processes via Monitoring of Buffer Levels", *Proc. of the 9th International Conference on Productivity & Quality Research*, Jerusalem, Israel, Jun. 25-28, 2000, pp. 340-347; Shmilovici A., Ben-Gal I., "Statistical Process Control for a Context Dependent Process Model", *Proc. of the Annual EURO Operations Research conference*, Budapest, Hungary, Jul. 16-19, 2000; Ben-Gal I., Shmilovici A., Morag G., "An Information Theoretic Approach for Adaptive Monitoring of Processes", ASI2000, *Proc. of The Annual Conference of ICIMS—NOE and IIMB*, Bordeaux, France, Sep. 18-20, 2000; Singer G. and Ben-Gal I., "A Methodology for Integrating Engineering Process Control and Statistical Process Control", *Proc. of The $16^{th}$ International Conference on Production Research*, Prague, Czech Republic. 29 Jul.-Aug. 3, 2001; and Ben-Gal I., Shmilovici A., "Promoters Recognition by Varying-Length Markov Models", Artificial Intelligence and Heuristic Methods for Bioinformatics, 30 September-12 October, San-Miniato, Italy. The contents of each of the above documents is hereby incorporated by reference.

SUMMARY OF THE INVENTION

According to a generalized aspect of the present invention there is thus provided an algorithm, which can analyze strings of consecutive symbols taken from a finite set. The symbols are viewed as observations taken from a stochastic source with unknown characteristics. Without a priori knowledge, the algorithm constructs probabilistic models that represent the classes, dynamics and interrelations within the data. It then monitors incoming data strings for compatibilities or incompatibilities with the models that were constructed. Compatibilities between the probabilistic model and the incoming strings are identified and analyzed to trigger appropriate actions such as correct classification. Incompatibilities between the probabilistic model and the incoming strings are identified and analyzed to trigger appropriate actions (application dependent).

According to a first aspect of the present invention there is provided apparatus for building a stochastic model of a data sequence, said data sequence comprising spatially related symbols selected from a finite symbol set, the apparatus comprising:

an input for receiving said data sequence, a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence.

Preferably, the tree reducer comprises a tree pruner for removing from said tree any node whose counter values are within a threshold distance of counter values of a preceding node in said tree.

Preferably, the various tree construction parameters are user definable. Thus, such tree construction parameters include threshold distance and tree construction parameters are user selectable. Preferably, said user selectable parameters further comprise a tree maximum depth.

Preferably, said tree construction parameters further comprise an algorithm buffer size Preferably, said tree construction parameters further comprise values of pruning constants.

Preferably, said tree construction parameters further comprise a length of input sequences.

Preferably, said tree construction parameters further comprise an order of input symbols.

Preferably, said tree reducer further comprises a path remover operable to remove any path within said tree that is a subset of another path within said tree.

Preferably, said sequential data is a string comprising consecutive symbols selected from a finite set.

The apparatus preferably further comprises an input string permutation unit for carrying out permutations and reorganizations of the input string using external information about a process generating said string.

Preferably, said string is a nucleic acid sequence.

Preferably, said string is a promoter and said tree is operable to identify other promoters.

Preferably, said string is a string of coding DNA, and said tree is operable to identify other coding strings.

Preferably, said string is a string of non-coding DNA, and said tree is operable to identify other non-coding strings.

Preferably, said string is a DNA string and said tree is operable to identify poly-A terminators.

Preferably, said string has a given property, and said tree is operable to identify other strings having said given property.

Preferably, said string is an amino-acid sequence and the symbols comprise at least some of the 20 amino-acids.

Preferably, said string is an amino acid string and said tree is operable to identify at least one of primary, secondary and three dimensional protein structure.

Preferably, said string has a given property, and said tree is operable to identify other strings having said given property.

Preferably, said nucleic acid sequence is a promoter sequence and another nucleic acid sequence is a non-promoter sequence, wherein said stochastic modeler is operable to build models of said promoter sequence and said non-promoter sequence and said comparator is operable to compare a third nucleic acid sequence with each of said models to determine whether said third sequence is a promoter sequence or a non-promoter sequence.

Preferably, said nucleic acid sequence is a coding sequence and another nucleic acid sequence is a non-coding sequence, wherein said stochastic modeler is operable to build models of said coding sequence and said non-coding sequence and said comparator is operable to compare a third nucleic acid sequence with each of said models to determine whether said third sequence is a coding sequence or a non-coding sequence.

Preferably, said nucleic acid sequence is a repetitive sequence and another nucleic acid sequence is a non-repetitive sequence, wherein said stochastic modeler is operable to build models of said repetitive sequence and said non-repetitive sequence and said comparator is operable to compare a third nucleic acid sequence with each of said models to determine whether said third sequence is a repetitive sequence or a non-repetitive sequence.

Preferably, said nucleic acid sequence is a non-coding sequence and another nucleic acid sequence is a coding sequence, wherein said stochastic modeler is operable to build models of said non-coding sequence and said coding sequence and said comparator is operable to compare a third nucleic acid sequence with each of said models to determine whether said third sequence is a non-coding sequence or a coding sequence.

Preferably, said nucleic acid sequence is an exon sequence, wherein said stochastic modeler is operable to build a model of said exon sequence and said comparator is operable to compare a second nucleic acid sequence with said model to determine whether said second sequence is an exon sequence.

Preferably, said nucleic acid sequence is an intron sequence, wherein said stochastic modeler is operable to build a model of said intron sequence and said comparator is operable to compare a second nucleic acid sequence with said model to determine whether said second sequence is an intron sequence.

Preferably, said stochastic model is refinable using further data sequences, thereby to define a structure of a common attribute of said data sequences.

According to a second aspect of the present invention there is provided apparatus for determining statistical consistency in spatially related data comprising a finite set of symbols, the apparatus comprising a sequence input for receiving said spatially related data, a stochastic modeler for producing at least one stochastic model from at least part of said spatially related data, and a comparator for comparing said stochastic model with a prestored model, thereby to determine whether there has been a statistical change in said data.

Preferably, said stochastic modeler comprises:

a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence.

Preferably, said prestored model is a model constructed using another part of said spatially related data.

Preferably, said comparator comprises a statistical processor for determining a statistical distance between said stochastic model and said prestored model.

Preferably, said comparator comprises a statistical processor for determining a difference in statistical likelihood between said stochastic model and said prestored model.

Preferably, said statistical distance is a relative complexity measure. The statistical distance may comprise an SPRT statistic, or an MDL statistic or a a Multinomial goodness of fit statistic or a Weinberger Statistic, or a KL statistic, or any other suitable statistic.

Preferably, said tree reducer comprises a tree pruner for removing from said tree any node whose counter values are within a threshold distance of counter values of a preceding node in said tree.

Preferably, said threshold distance, and other tree construction parameters, are user selectable.

Preferably, tree construction parameters further comprise a tree maximum depth.

Preferably, tree construction parameters further comprise an algorithm buffer size.

Preferably, tree construction parameters further comprise values of pruning constants.

Preferably, user selectable parameters further comprise a length of input sequences.

Preferably, tree construction parameters further comprise an order of input symbols.

Preferably, said tree reducer further comprises a path remover operable to remove any path within said tree that is a subset of another path within said tree.

Preferably, said data comprises a nucleic acid sequence.

Preferably, said data comprises an amino-acid sequence.

Preferably, said sequential data is an output of a medical sensor sensing bodily functions.

Preferably, said nucleic acid sequence is a promoter sequence and another nucleic acid sequence is a non-promoter sequence, wherein said stochastic modeler is operable to build models of said promoter sequence and said non-promoter sequence and said comparator is operable to compare a third nucleic acid sequence with each of said models to determine whether said third sequence is a promoter sequence or a non-promoter sequence.

Preferably, said nucleic acid sequence is a coding sequence and another nucleic acid sequence is a non-coding sequence, wherein said stochastic modeler is operable to build models of said coding sequence and said non-coding sequence and said comparator is operable to compare a third nucleic acid sequence with each of said models to determine whether said third sequence is a coding sequence or a non-coding sequence.

Preferably, said nucleic acid sequence is a repetitive sequence and another nucleic acid sequence is a non-repetitive sequence, wherein said stochastic modeler is operable to build models of said repetitive sequence and said non-repetitive sequence and said comparator is operable to compare a third nucleic acid sequence with each of said models to determine whether said third sequence is a repetitive sequence or a non-repetitive sequence.

Preferably, said nucleic acid sequence is a non-coding sequence and another nucleic acid sequence is a non-non-coding sequence, wherein said stochastic modeler is operable to build models of said non-coding sequence and said non-non-coding sequence and said comparator is operable to compare a third nucleic acid sequence with each of said models to determine whether said third sequence is a non-coding sequence or a non-non-coding sequence.

Preferably, said data sequence comprises image data of a first image.

Preferably, said distance is indicative of a statistical distribution within said image.

Preferably, the apparatus further comprises an image comparator for comparing said statistical distribution with a statistical distribution of another image.

Preferably, the other image is of a same view as said first image taken at a different time, said distance being indicative of time dependent change.

Preferably, said image data comprises medical imaging data, said statistical distance being indicative of deviations of said data from an expected norm.

The embodiments are preferably applicable to a database to perform data mining on said database.

Preferably, said stochastic model is constructed from descriptions of a plurality of enzymes for carrying out a given task, said model thereby providing a generic structural description of an enzyme for carrying out said task.

Preferably, the model is usable to analyze results of a nucleic acid micro array.

Preferably, the model is usable to analyze results of a protein microarray.

According to a third aspect of the present invention there is provided a method of designing a protein for carrying out a predetermined task, the method comprising:

taking a plurality of proteins known to carry out said predetermined task, constructing a stochastic model using an amino acid sequence of said plurality of proteins, using said stochastic model to predict a protein sequence.

According to a fourth aspect of the present invention there is provided a method of designing a protein for carrying out a predetermined task, the method comprising:

taking a plurality of proteins known to carry out said predetermined task, constructing a stochastic model using the 3D structure of said plurality of proteins, using said stochastic model to determine a protein structure.

According to a fifth aspect of the present invention there is provided a method of distinguishing between biological sequences of a first kind and biological sequences of a second kind, each kind being expressible in terms of a same finite set of symbols, the method comprising:

obtaining a statistically significant set of sequences of said first kind and building a stochastic model thereof, obtaining a statistically significant set of sequences of said second kind and building a stochastic model thereof, and taking a further sequence and comparing it with each stochastic model to determine whether it belongs to either set.

Preferably, said biological sequences are nucleic acid sequences.

Preferably, said biological sequences are amino acid sequences.

Preferably, the sequences of said first kind are promoter sequences.

Alternatively or additionally, the sequences of said first kind are coding and the sequences of said second kind are non-encoding sequences.

Preferably, the sequences are non-species specific, thereby constructing models which are non-species specific.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 1A is a tree diagram describing general methodologies for pattern classification, FIG. 1D is a simplified diagram showing the interrelationships between different modeling and characterization methods related to Statistical Process Control and Change Point areas. These areas are related to pattern classification and are relevant to the presented invention. The figure specifically shows where the present embodiments fit in with the prior art.

FIG. 3a is a context tree constructed from a simulator in accordance with an embodiment of the present invention, FIG. 3b is a context tree for 238 *E Coli* promoters constructed in accordance with an embodiment of the present invention, FIGS. 7-11 are simplified diagrams of context trees at various stages of their construction, FIG. 12 is a state diagram of a stochastic process that can be monitored to demonstrate operation of the present embodiments, and FIGS. 13-23 show various stages and graphs in modeling and attempting to control the process of FIG. 12 according to the prior art and according to the present invention.

DESCRIPTION OF THE PREFERRED EMBODIMENTS

Figure 1B:
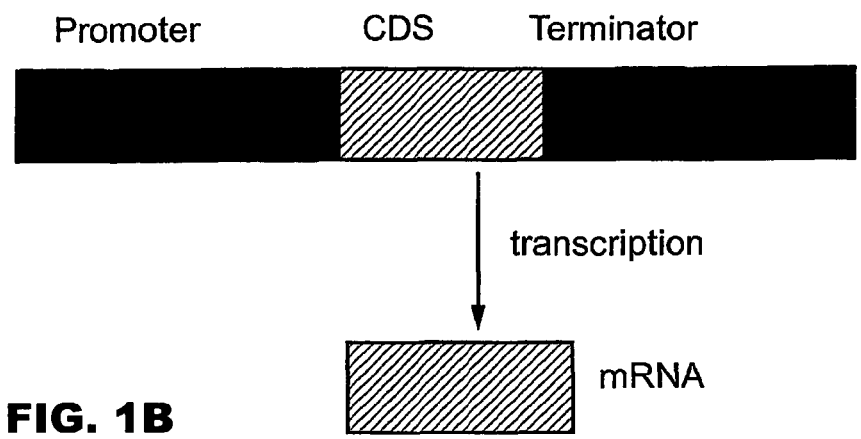
FIG. 1B is a schematic diagram of a prokaryotic gene sequence.
Figure 1C:
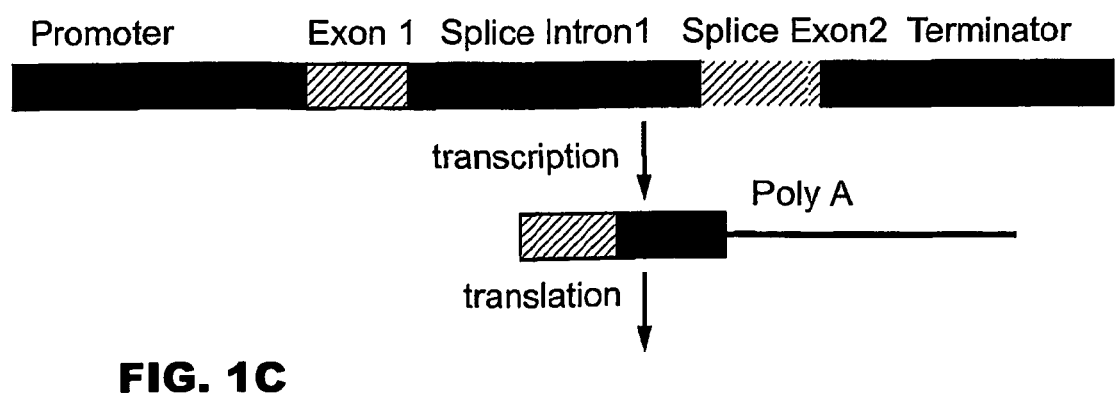
FIG. 1C is a schematic diagram of a eukaryotic gene sequence.

In the present embodiments, a model-generic pattern classification method and apparatus are introduced for the control of state-dependent data. The method is based on the context-tree model that was proposed for data-compression purposes and later for prediction and identification. The context-tree model comprises an irreducible set of conditional probabilities of output symbols given their contexts. It offers a way of constructing a simple and compact model to a sequence of symbols including those describing complex, non-linear processes such as HMM of higher order. An algorithm is used to construct a context tree, and preferably, the algorithm of the context-tree generates a minimal tree, depending on the input parameters of the algorithm, that fits the data gathered.

The present embodiments are based on a modified context-tree that belongs to the above category. The suggested model is different from the models discussed in the background in respect of
  i) in its construction principles;
  ii) its ability to find and compute what we call "partial contexts" and their probabilities—that were found to have vital importance in Biology classification applications; and
  iii) in the suggested distance measures between different trees.

In order to monitor the statistical attributes of a process, the first embodiments compare two context trees at any time during monitoring. For example, in certain types of analysis, in particular DNA analysis, it is possible to divide a sequence into subsequences and build trees for each. Thus, it is possible to compare several pairs of trees at once with a monitor tree and a reference tree formed from monitor and reference data respectively for each pair. The comparison may be carried out by comparing the likelihood density of the given sequence according to each of the trees and then classifying the sequence upon a given threshold. The first context tree is a reference tree that belongs to a certain type of class, that is to say a model of how the classified data is expected to behave. There might be several context trees of this type—each of which belonging to a known class of sequencesm, such as coding, promoters etc. The second context tree is a monitored tree, generated periodically from a sequence of an unknown class, which needs to be classified. The tree parameters are often unknown and need to be estimated. A preferred embodiment uses maximum likelihood estimates and likelihood ratios (or log-likelihood ratios) to measure a relative 'distance' between these two trees with respect to a user-predetermined threshold. There are number of statistics that can be used in addition to or as an alternative to likelihood ratios, as will be explained in greater detail below.

As will be explained below, in a first stage in certain of the embodiments, such as for DNA analysis, a string may be divided into a plurality of substrings for each of which a tree is built. Then several pairs of these trees are compared simultaneously wherein one of the trees in each pair is a reference tree and is generated from a reference or training data set, and the monitored tree is generated from the monitored data set.

In DNA applications in general, in the first stage groups of strings are selected that share common properties or functionality—such as promoters/binding-sites/exons and introns/coding vs non-coding/amino-acids that have the same secondary (or higher) structure/proteins or enzymes that have certain functionally—e.g., effects on patient health etc. The groups are taken from a training or learning set.—From the training set a tree model is built for each group of strings. In the second stage, however, the tree model is generally used for RECOGNITION or PREDICTION over a "test set" of strings. Thus, it is possible to recognize if a given string belongs to a group of promoters/coding DNA/noncoding DNA/certain group of proteins with certain important properties/ etc or the model may try to predict certain properties of a given string (e.g., the secondary structure of a given sequence of amino acids). Usually this is done by computing the likelihood of that given string based on the tree models, thus, if (*) Pr{string| Tree No 2}>Pr{string| Tree No 1}>Pr{string| Tree No 4}> . . . we can say that the most likely that the string is recognize to belong to the group that is described by Tree 2 etc. In fact such a query is essentially Bayesian estimation—in the general case if we have an apriori knowledge regarding the distribution of the groups denoted by P{Tree Model}, in the set—then the likelihood are computed by Bayes theorem: Pr{Tree model| string}=P{string| Tree model}*P{Tree-model}/P{string}. Sometimes, if a priori knowledge of the distribution of groups in the data is not available, then we may assign a uniform probability to all P{Tree Model} which is equivalent to using the simpler form (*) of the likelihood function.

In certain of the embodiments, Similar models may differ based on certain changes of the model construction or the classification algorithm, such as: i) position dependence/inhomogeneous models; ii) mixed backward/forward algorithms; iii) permutation and reorganization of input strings—thus, adding outside "information"; iv) type of levels—e.g., amino acids/nucleotides/proteins, v) divisions of substrings, etc.—some of these modified models are described below.

A preferred embodiment of the present invention, hereinafter Context-Tree classification (CTC) has several particular advantages. Firstly, the embodiment learns the dynamics and the underlying distributions within a data string being monitored as part of model building. Such learning may be done without requiring a priori information, hence categorizing the embodiment as model-generic. Secondly, the embodiment extends the current limited scope of pattern classification applications to state-dependent classes with varying length order and partial leafs, as will be explained in more detail below. Thirdly, the embodiment provides convenient monitoring of discrete data.

A second embodiment uses the Kullback-Leibler (KL) statistic to measure a relative distance between the two compared trees and derive an asymptotic distribution of the relative distance. Monitoring the KL estimates with respect to the asymptotic distribution, indicates whether there has been any significant change of characteristics in the input data.

Other embodiments measure the stochastic complexity, or other statistic measures to measure a relative distance between the two compared trees and derive an asymptotic distribution of the relative distance. Monitoring the analytic distribution of the stochastic complexity, indicates whether there has been a significant change in the characteristics of the input data that requires a different classification. An advantage of the second embodiment over the first one is that it sometimes requires less monitored data in order to produce satisfactory results.

Other possible statistics that may be used to measure the distance between tree models include the following:

Wald's sequential probability ratio testing (SPRT): Wald's test is implemented both in conventional CUSUM and change-point methods and has analytical bounds developed based on the type-I and type-II errors. The advantages of this statistic are that one can detect the exact change point and apply a sequential sample size comparison between the reference and the monitored tree.

MDL (Minimal Description Length): The MDL is the shortest description of a given model and data string by the minimum number of bits needed to encode them. Such a measure may be used to test whether the reference 'in-control' context-tree and the monitored context-tree are from the same distribution.

Multinomial goodness of fit tests: Several goodness of fit tests may be used for multinomial distributions. In general, they can be applied to tree monitoring since any context tree can be represented by a joint multinomial distribution of symbols and contexts. One of the most popular tests is the Kolmogorov-Smirnov (KS) goodness of fit test. Another important test that can be used for CC is the Andersen-Darling (AD) test. This test is superior to the KS test for distributions that mainly differ in their tail (i.e., it provides a different weight for the tail).

Weinberger's Statistic: proposes a measure to determine whether the context-tree constructed by context algorithm is close enough to the "true" tree model (see eqs. (18), (19) in their paper). The advantage of such a measure is its similarity to the convergence formula (e.g., one can find bounds for this measure based on the convergence rate and a chosen string length N). However, the measure has been suggested and is more than adequate for coding purposes since it assumes that the entire string N is not available.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Reference is now made to FIG. 1D, which is a chart showing characterization of SPC methods. We note that the embodiment of the context-tree classification (CTC) is related to the embodiment of context-based statistical process control (CSPC). In fact, both embodiments are based on the suggested context-tree model, however, each of which has a different area of applications—CTC for pattern classification and CSPC for statistical process control—we thereafter use these terms interchangeably. FIG. 1D shows how the context-based SPC (CSPC) and, thus, the CTC embodiments of the present invention relate to existing methods of SPC methods.

Figure 2:
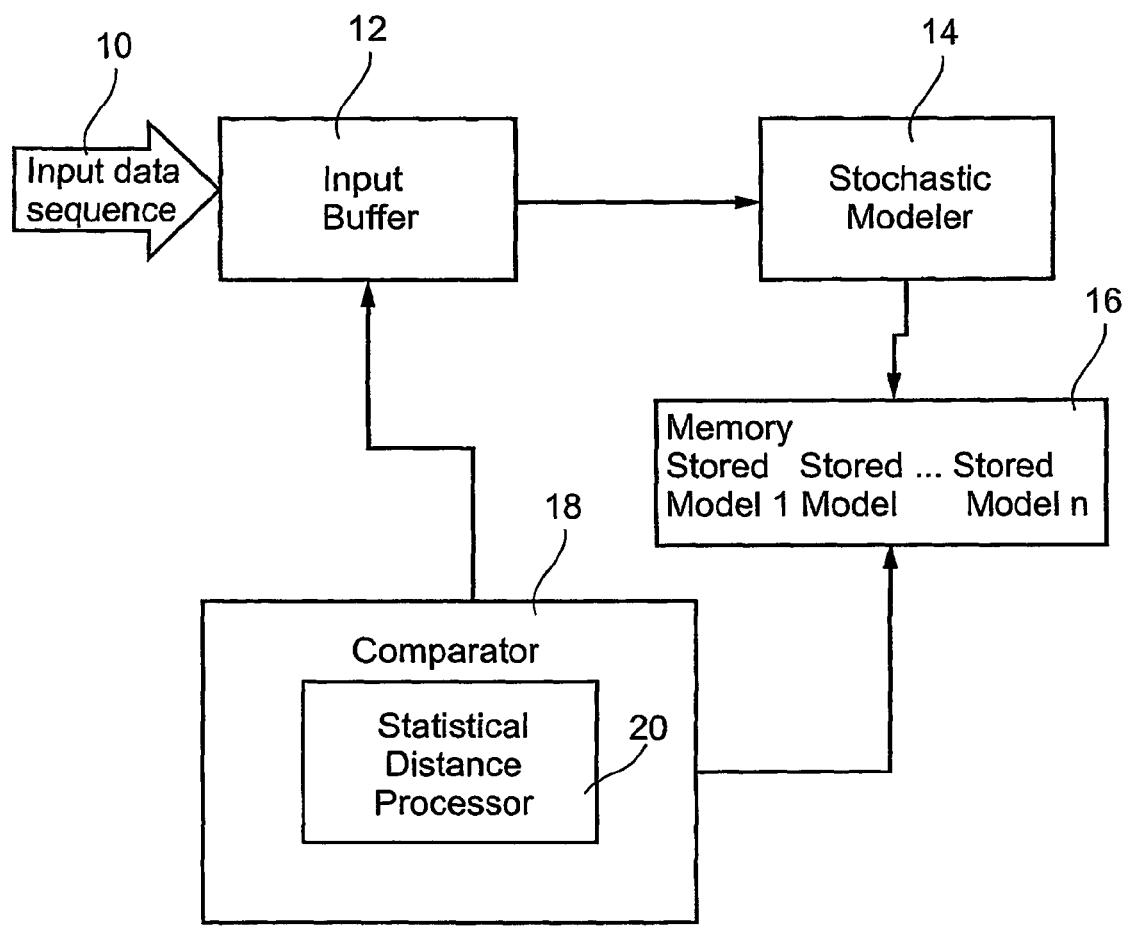
FIG. 2 is a block diagram of a device for monitoring an input sequence according to a first preferred embodiment of the present invention.

Reference is now made to FIG. 2, which is a simplified block diagram showing a generalized embodiment of the present invention. In the embodiment of FIG. 2, an input data sequence 10 arrives at an input buffer 12. A stochastic modeler 14 is able to use the data arriving in the buffer to build a statistical model or measure that characterizes the data. The building process and the form of the model will be explained in detail below.

The modeler 14 does not necessary build models for all of the data. During the course of processing, it may build a single model or it may build successive models on successive parts of the data sequence. The model or models are stored in a memory 16. A comparator 18 comprises a statistical distance processor 20, which is able in one embodiment to make a statistical distance measurement between a model generated from current data and a prestored model. In a second embodiment the statistical distance processor 20 is able to make a statistical distance measurement of the distance between two or more models generated from different parts of the same data. In a third embodiment, the statistical distance processor 20 is able to make a statistical distance measurement of the distance between a pre-stored model and a data sequence. In either embodiment, the statistical measure is used by the comparator 18 to determine whether (or not) a statistically significant change in the data characteristics has occurred.

As will be described below, the comparator 18 may use the log-likelihood ratio or the KL statistical distance measure. KL is particularly suitable where the series is stationary and sufficiently long. Other measures are more appropriate where the series is space or otherwise dependent.

Reference is now made to FIG. 3, which is a simplified diagram showing a prior art model that can be used to represent statistical characteristics of data. In this section, we introduce the context trees model for state-dependent data and the concepts of its construction algorithm following the definitions and notations in the relevant citations, and. A detailed walk-through example presenting the context-tree construction is given in FIGS. 7-11 and Tables A1 A2.

Consider a sequence (string) of observations $x^N = x_1, \ldots, x_N$, with elements $x_t$, $t=1, \ldots, N$ defined over a finite symbol set, X, of size d. In practice, this string can represent a realization sequence of a discrete variable drawn from a finite-set. Particularly, the discrete variable can be a queue length in a queuing system, such as the number of parts in a buffer in a production line. For a finite buffer capacity c, the 'finite symbol set' (of possible buffer levels) is $X = \{0, 1, 2, \ldots, c\}$ and d, the symbol-set size, is thus equal to $d = c+1$. For instance, the string $x^6 = 1, 0, 1, 2, 3, 3$ represents a sequence of six consecutive observations of the buffer level (number of parts) in a production line with buffer capacity of $c=3$.

A family of probability measures $P_N(x^N)$, $N=0, 1, \ldots$ is defined over the set $\{X^N\}$ of all stationary sequences of length N, such that the marginality condition $$\sum_{x \in X} P_{N+1}(x^N x) = P_N(x^N) \quad (2.1)$$

holds for all N; $x^N x = x_1, \ldots, x_N, x$; and $P_0(x^0) = 1$ where $x^0$ is the empty string. For simplification of notations, the subindex will be omitted, so that $P_N(x^N) \equiv P(x^N)$ One could opt to find a model that assigns the probability measure (2.1). A possible finite-memory source model of the sequences defined above is the Finite State Machine (FSM), which assigns a probability to an observation in the string based on a finite set of states. Hence, the FSM is characterized by the transition function, which defines the state for the next symbol, $$s(x^{N+1}) = f(s(x^N), x_{N+1}) \quad (2.2)$$

where $s(x^N) \in \Gamma$ are the states with a finite state space $|\Gamma| = S$; $s(x^0) = s_0$ is the initial state; and $f: \Gamma \times X \to \Gamma$ is the state transition map of the machine. The FSM is then defined by $S \cdot (d-1)$ conditional probabilities, the initial state $s_0$, and the transition function. The set of states of an FSM should satisfy the requirement that the conditional probability to obtain a symbol given the whole sequence is equal to the conditional probability to obtain the symbol given the past state, implying that $$P(x|x^N) = P(x|s(x^N)) \quad (2.3)$$

A special case of FSM is the Markov process. The Markov process satisfies (2.2) and is distinguished by the property that for a kth-order Markov process $s(x^N) = x_N, \ldots, x_{N-k+1}$. Thus, reversed strings of a fixed length k act as source states. This means that the conditional probabilities of a symbol given all past observations (2.3) depend only on a fixed number of observations k, which defines the order of the process. However, even when k is small, the requirement for a fixed order can result in an inefficient estimation of the probability parameters, since some of the states often depend on shorter strings than the process order. On the other hand, increasing the Markov order to find a best fit results in an exponential growth of the number of states, $S = d^k$, and, consequently, of the number of conditional probabilities to be estimated.

An alternative model to the Markovian is the context-tree that was suggested for data compression purposes and modified later. The tree presentation of a finite-memory source is advantageous since states are defined as contexts—graphically represented by branches in the context-tree with variable length—and hence, requires less estimation efforts than those required for a Markov presentation. The context-tree is an irreducible set of conditional probabilities of output symbols given their contexts. The tree is conveniently estimated by context algorithm. The algorithm generates an asymptotically minimal tree fitting the data. The attributes of the context-tree along with the ease of its estimation make it suitable for a model-generic classifier, as seen later.

A context, $s(x^t)$, in which the "next" symbol in the string $x_{t+1}$ occurs is defined as the reversed string (we use the same notation for contexts as for the FSM states, since here, they follow similar properties), $$s(x^t) = x_t, \ldots, x_{max\{0, t-k+1\}} \quad (2.4)$$

for some $k \geq 0$, not necessarily the same for all strings (the case $k=0$ is interpreted as the empty string $s_0$). The string is truncated since the symbols observed prior to $X_{t-k+1}$ do not affect the occurrence probability of $X_{t+1}$. For the set of optimal contexts, $\Gamma = \{s: \text{shortest contexts satisfying (2.3)}\}$, k is selected to attain the shortest contexts for which the conditional probability of a symbol given the context is practically equal to the conditional probability of that symbol given the whole data, i.e., nearly satisfying (2.3). Thus, an optimal context, $s \in \Gamma$, acts as a state of the context-tree, and is similar to a state in a regular Markov model of order k. However, unlike the Markov model, the lengths of various contexts do not have to be equal and one does not need to fix k such that it accounts for the maximum context length. The variable context lengths in the context-tree model result in fewer parameters that have to be estimated and, consequently, require less data to identify the source. It is noted, however, that the optimal contexts model does not necessarily satisfy equation (2.2), since the new state $s(x^{N+1})$ can be longer than $s(x^N)$ by more than one symbol.

Using the above definitions, a description of the context-tree follows. A context-tree is an irreducible set of probabilities that fits the symbol sequence $x^N$ generated by a finite-memory source. The tree assigns a distinguished optimal context for each element in the string, and defines the probability of the element, $x_t$, given its optimal context. These probabilities are used later for classification and identification—comparing between sequences of observations and identifying whether they belong to the same class. Graphically, the context-tree is a d-ary tree which is not necessarily complete and balanced. Its branches (arcs) are labeled by the different symbol types. Each node contains a vector of d conditional probabilities of all symbols $x \in X$ given the respective context (not necessarily optimal), which is represented by the path from the root to that specific node. An optimal context $s \in \Gamma$ of an observation $x_t$ is represented by the path starting at the root, with branch $x_t$ followed by branch $x_{t-1}$ and so on, until it reaches a leaf or a partial leaf FIG. 3 exemplify a context-tree that was constructed from a sequence of observed buffer levels in a production line. Since in this case the buffer has a finite capacity of $c=2$, there are $d=3$ symbol types, where observation, $x_t \in \{0, 1, 2\}$, refer to the number of parts in the buffer at time t. Using the context algorithm, $S=5$ optimal contexts are found (marked by bolded frame), thus, the set of optimal contexts is a collection of reversed strings Γ={0,2,102,1010,10101} (read from left to right). The context 1010 is a partial leaf.

Consider the string $x^6$=1,2,0,1,0,1, which is generated from the tree source in FIG. 3. Employing the above definitions, the optimal context of the next element, $x_7$=0, is $s(x^6)$= 1,0,1,0, i.e., following the reverse string from the root until reaching an optimal context. Accordingly, the probability of $x_7$ given the context is $P(x_7$=0|$s(x^6))$=0.33. Note that had we used a Markov chain model with maximal dependency order, which is k=5 (the longest branch in the tree), we would need to estimate the parameters of $3^5$=243 states (instead of the five optimal contexts in the context-tree of FIG. 2), although most of them are redundant.

The conditional probabilities of symbols given the optimal contexts, P(x|s) x∈X, s∈Γ, and the marginal probabilities of optimal contexts P(s), s∈Γ are estimated by the context algorithm. The joint probabilities of symbols and optimal contexts, P(x,s), x∈X, s∈Γ, represent the context-tree model and are used to derive the classifying algorithm. This model might be only an approximated description of the real generating source, but it is often appropriate for practical purposes.

Figure 4:
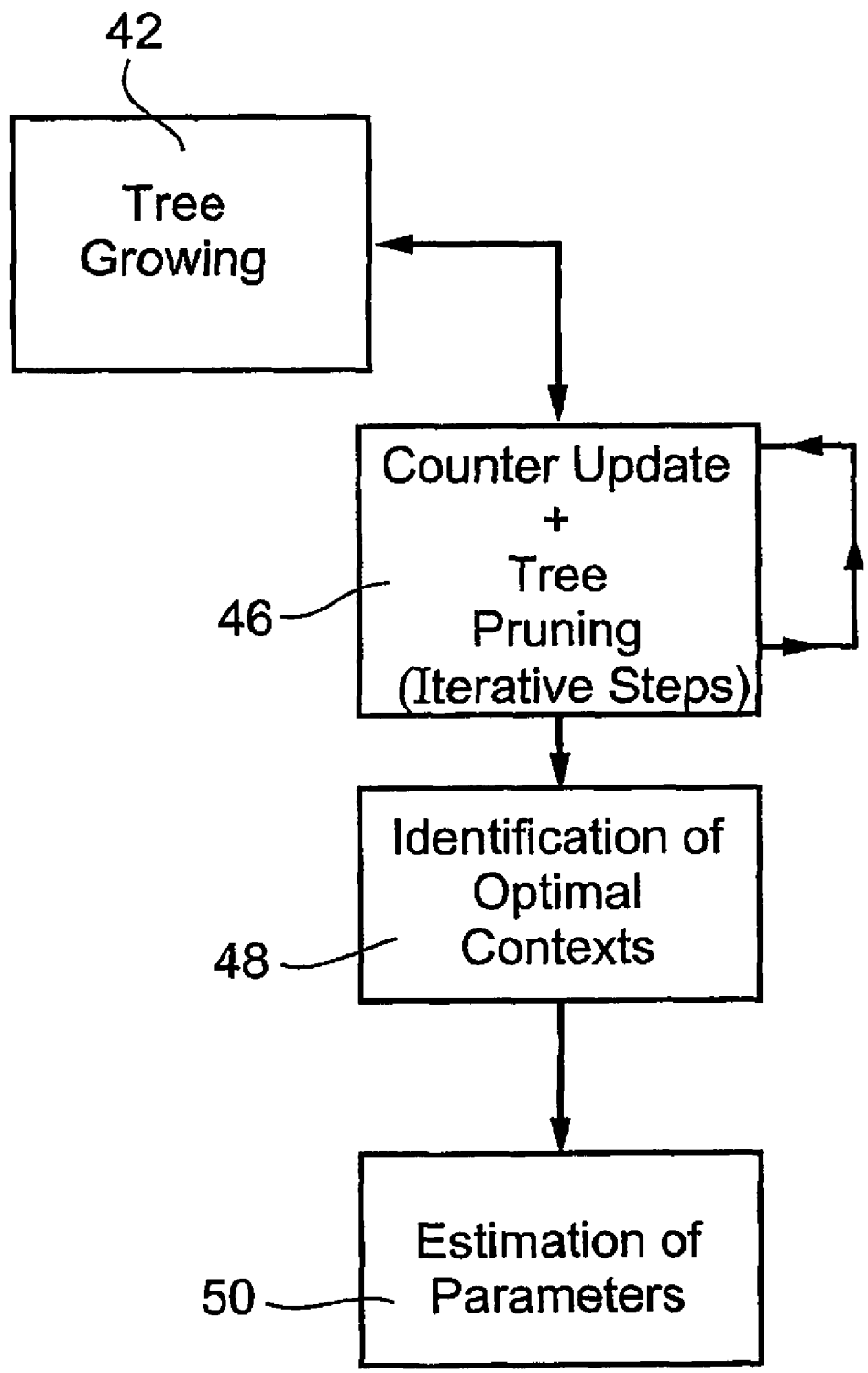
FIG. 4 is a simplified flow diagram showing a process of building an optimal context tree according to embodiments of the present invention.

Reference is now made to FIG. 4, which is a simplified schematic diagram showing stages of an algorithm for producing a context tree according to a first embodiment of the present invention. The construction algorithm of FIG. 4 is an extension of the Context algorithm referred to above. The algorithm preferably constructs a context-tree from a string of N symbols and estimates the marginal probabilities of contexts and the conditional probabilities of symbols given contexts. The algorithm comprises five stages as follows: two concomitant stages of tree growing 42 and iteratively counter updating and tree pruning 46; a stage of optimal contexts identification 48; and a stage of estimating context-tree probability parameters 50.

In the tree growing stage 42, a counter context-tree, $T_t$ 0≦t≦N, is grown up to a maximum depth m. Each node in $T_t$ contains d counters—one for each symbol type. The counters, n(x|s), denote the conditional frequencies of the symbols x∈X in the string $x^t$ given the contexts. Concomitantly with the tree growth stage 42, the counter updating and tree pruning stage 46 ensures that the counter values n(x|s) are updated according to symbol occurrences as will be explained in more detail hereinbelow. The counter context tree is iteratively pruned along with counter updating to acquire the shortest reversed strings, thereby in practical terms to satisfy equation 2.3, it being noted that exact equality is not achieved. In the following stage, selection of optimal contexts 48, a set of optimal contexts Γ is obtained, based on the pruned counter context tree. In the estimation stage 50, the estimated conditional probabilities of symbols given optimal contexts P̂(x|s), x∈X s∈Γ and the estimated marginal probabilities of optimal contexts P̂(s), s∈Γ are derived. As discussed in more detail hereinbelow, both P̂(x|s) and P̂(s) are approximately multinomially distributed and used to obtain the CSPC control limits. The estimated joint probabilities of symbols and optimal contexts, P̂(x, s)=P̂(x|s)·P̂(s), x∈X, s∈Γ, are then derived and represent the context-tree in its final form. It is noted that the term "counter context-tree" is used to refer to the model as it results from the first three stages in the algorithm and the term "context-tree" is used to refer to the result of the final stage, which tree contains the final set of optimal contexts and estimated probabilities.

Returning now to FIG. 2, and once a model is obtained for incoming data, the model is compared by comparator 18 with a reference model, or more than one reference model, which may be a model of earlier received data such as training data or may be an a priori estimate of statistics for the data type in question or the like.

In the following, examples are given based on measurements using the KL statistic. However, the skilled person will appreciated that other statistical measures may be used, including but not restricted to those mentioned hereinabove.

A researcher proposed a measure for the relative 'distance' or the discrimination between two probability mass functions Q(x) and Q0(x):

$$K(Q(x), Q_0(x)) = \sum_{x \in X} Q(x) \log \frac{Q(x)}{Q_0(x)} \geq 0 \quad (3.1)$$

The measure, now known as the Kullback Liebter (KL) measure, is positive for all non-identical pairs of distributions and equals zero iff (if and only if) Q(x)=$Q_0$(x) for every x. The KL measure is a convex function in the pair (Q(x),$Q_0$(x)), and invariant under all one-to-one transformations of the data. Kullback has shown that the KL distance (multiplied by a constant), between a d-category multinomial distribution Q(x) and its estimated distribution Q̂(x), is asymptotically chi-square distributed with d−1 degrees of freedom:

$$2N \cdot K(\hat{Q}(x), Q(x)) \to \sum_{x \in X} \frac{(n(x) - NQ(x))^2}{NQ(x)} \sim \chi^2_{d-1},$$

where N is the size of a sample taken from the population specified by Q(x); n(x) is the frequency of category (symbol type) x in the sample, $$\sum_{x \in X} n(x) = N;$$

and Q̂(x)=n(x)/N is the estimated probability of category (symbol type) x.

The KL measure for the relative 'distance' between two joint probability mass functions Q(xy) and $Q_0$(xy) can be partitioned into two terms, one representing the distance between the conditioning random variable and the other representing the distance between the conditioned random variable:

$$K(Q(x, y), Q_0(x, y)) = \quad (3.3)$$

$$\sum_{y \in S} Q(y) \log \frac{Q(y)}{Q_0(y)} + \sum_{y \in S} Q(y) \sum_{x \in X} Q(x|y) \log \frac{Q(x|y)}{Q_0(x|y)}$$

In the present embodiments the comparator 18 preferably utilizes the KL measure to determine a relative distance between two context-trees. The first tree, denoted by $\hat{P}_i$(x,s), represents the monitored distribution of symbols and contexts, as estimated from a string of length N at the monitoring time i=1,2, ... The second tree, denoted by $P_0$(x,s), represents the 'in-control' reference distribution of symbols and contexts. The reference distribution is either known a priori or can be effectively estimated by the context algorithm from a long string of observed symbols as will be discussed in greater detail below. In the latter case, the number of degrees of freedom is doubled.

Utilizing what is known as the minimum discrimination information (MDI) principle the context algorithm preferably generates a tree of the data being monitored, the tree having a similar structure to that of the reference tree. Maintaining the same structure for the current data tree and the reference tree permits direct utilization of the KL measure.

Now, new observations are constantly being collected and may be used for updating the current data tree, in particular the counters thereof and thus updating the statistics represented by the tree. A significant change in the structure of the tree may be manifested in the tree counters and the resulting probabilities.

Using equation (3.3) above, it is possible to decompose the KL measured distance between the current data context-tree and the reference context-tree (both represented by the joint distributions of symbols and contexts) into a summation involving two terms as follows:

$$K(\hat{P}_i(x,s), P_0(x,s)) = \qquad (3.4)$$
$$\sum_{s \in \Gamma} \hat{P}_i(s) \log \frac{\hat{P}_i(s)}{P_0(s)} + \sum_{s \in \Gamma} \hat{P}_i(s) \sum_{x \in X} \hat{P}_i(x|s) \log \frac{\hat{P}_i(x|s)}{P_0(x|s)}.$$

Of the two terms being summated, one measures the KL distance between the trees' context probabilities, and the other measures the KL distance between the trees' conditional probabilities of symbols given contexts.

Under the null hypothesis that the monitored tree $\hat{P}_t(x,s)$ is generated from the same source that generated, $P_0(x,s)$ and by using the multinomial approximation referred to above, it is possible to derive an asymptotic probability density function of the KL measure between $\hat{P}_t(x,s)$ and $P_0(x,s)$, i.e., $$K(\hat{P}_i(x,s), P_0(x,s)) \rightarrow \qquad (3.5)$$
$$\frac{1}{2N}\chi^2_{S-1} + \sum_{s \in \Gamma}\hat{P}_i(s) \cdot \frac{1}{2n(s)}\chi^2_{d-1} =$$
$$\frac{1}{2N}\chi^2_{S-1} + \sum_{s \in \Gamma}\frac{n(s)}{N} \cdot \frac{1}{2n(s)}\chi^2_{d-1} =$$
$$\frac{1}{2N}\chi^2_{S-1} + \frac{1}{2N}\sum_{s \in \Gamma}\chi^2_{d-1} =$$
$$\frac{1}{2N}(\chi^2_{S-1} + \chi^2_{S(d-1)}) = \frac{1}{2N}\chi^2_{Sd-1},$$

where n(s) is the frequency of an optimal context $s \in \Gamma$ in the string; N is the size of the monitored string; S is the number of optimal contexts; and d is the size of the symbol set. As mentioned above, if the reference tree has to be estimated, the number of degrees of freedom may be doubled. Thus, the KL statistic for the joint distribution of the pair $(X,\Gamma)$ is asymptotically chi-square distributed with degrees of freedom depending on the number of symbol types and the number of optimal contexts. The result is of significance for the development of control charts for state-dependant discrete data streams based on the context-tree model.

Now, given a type I error probability $\alpha$, the control limits for the KL statistic are given by, $$0 \leq 2N \cdot K(\hat{P}_i(x,s), P_0(x,s)) \leq \chi^2_{Sd-1, 1-\alpha}. \qquad (3.6)$$

Thus, the upper control limit (UCL) is the $100(1-\alpha)$ percentile of the chi-square distribution with (Sd−1) degrees of freedom.

The control limit (3.6) has the following, advantageous, characteristics:
i) It is a one-sided bound; if the KL value is larger than the UCL, the process is assumed to be 'out-of-control' for a given level of significance.
ii) The control limit lumps together all the parameters of the context-tree, in contrast with traditional SPC where each process parameter is controlled separately. Nevertheless, the KL statistic of the tree can be easily decomposed to monitor separately each node in the context-tree. This can be beneficial when looking for a cause of an 'out-of-control' signal.
iii) If Sd is large enough, the KL statistic is approximately normally distributed. Hence, conventional SPC charts can be directly applied to monitor the proposed statistic.

A basic condition for applying the KL statistic to sample data requires that $P_0(x|s) > 0$, $\forall x \in X$, $\forall s \in \Gamma$. Such a constraint may be satisfied with the predictive approach, i.e., $$\hat{P}(x|s) = \frac{n(x|s) - \sum_{b \in X} n(x|sb) + 1/2}{n(s) + d/2} \quad \forall x, b \in X, s \in \Gamma$$

where all probability values assigned to any of the symbol types are strictly positive, in contrast to the non-predictive approach:

$$\hat{P}(x|s) = \frac{n(x|s) - \sum_{b \in X} n(x|sb)}{n(s)} \quad \forall x, b \in X, s \in \Gamma$$

by defining $$\frac{0}{0} \equiv 0.$$

The choice among these alternative procedures, depends both on the knowledge regarding the system states and on the length of the string used to construct the context-tree. However, in the latter non-predictive case, the number of degrees of freedom is adapted according to the number of categories that are not equal to zero, thus, subtracting the zero-probability categories when using the non-predictive approach.

Another example for a distance measure between two tree models is the use of log-likelihood ratios. This example considers an application of pattern recognition of *E. coli* promoters. The details of the experiment are listed as follows.

The 238 DNA strings of size 12 from a given database were converted to strings of numbers, and encode such that: "A"=1; "C"=2; "G"=3; "T"=4. A special version of the context-tree construction algorithm "cont12" was adapted for DNA sequences of size 12. It was adapted such that, the tree construction will use only contexts of length up to 5, and that the context buffer will be reset every time it reaches the size eleven. Thus, effectively, each appearance of a size 12 promoter will update the statistics of the context tree, and grow a tree with up to a depth of 5 levels (maximum context length of 5). The tree construction parameters were not optimized since it was conducted mainly for illustration purpose.

Reference is now made to FIG. 3b. The 238 number stings were concatenated to one large string "s". A 5 levels context tree was identified from the 238 promoter DNA by using defalt tree parameters. The likelihood of subsequences given the context trees can be computed for promoter and nonpromoter sequences. For example, the probability of the string GCTTA, according to the context tree in FIG. 3b, is calculated by parssing the string to identified contexts P{GCTTA}=P(G)*P(C|G)*P(T|GC)*P(T|GCT)*P(A|GCTT)=(see the context tree in FIG. 3b)=P(G)*P(C|G)*P(T)*P(T|T)*P(A|CTT)=0.4136*0.2164*0.3988*0.3589*0.5385.

As explained above, the distance measure between two models for a given string is obtain by computing the likelihood of that given string based on the tree models, thus, if (*) Pr{string| Tree No 2}>Pr{string| Tree No 1}>Pr{string| Tree No 4}> . . . one can say that the most likely that the string is recognize to belong to the group that is described by Tree 2 etc.

Figure 5A:
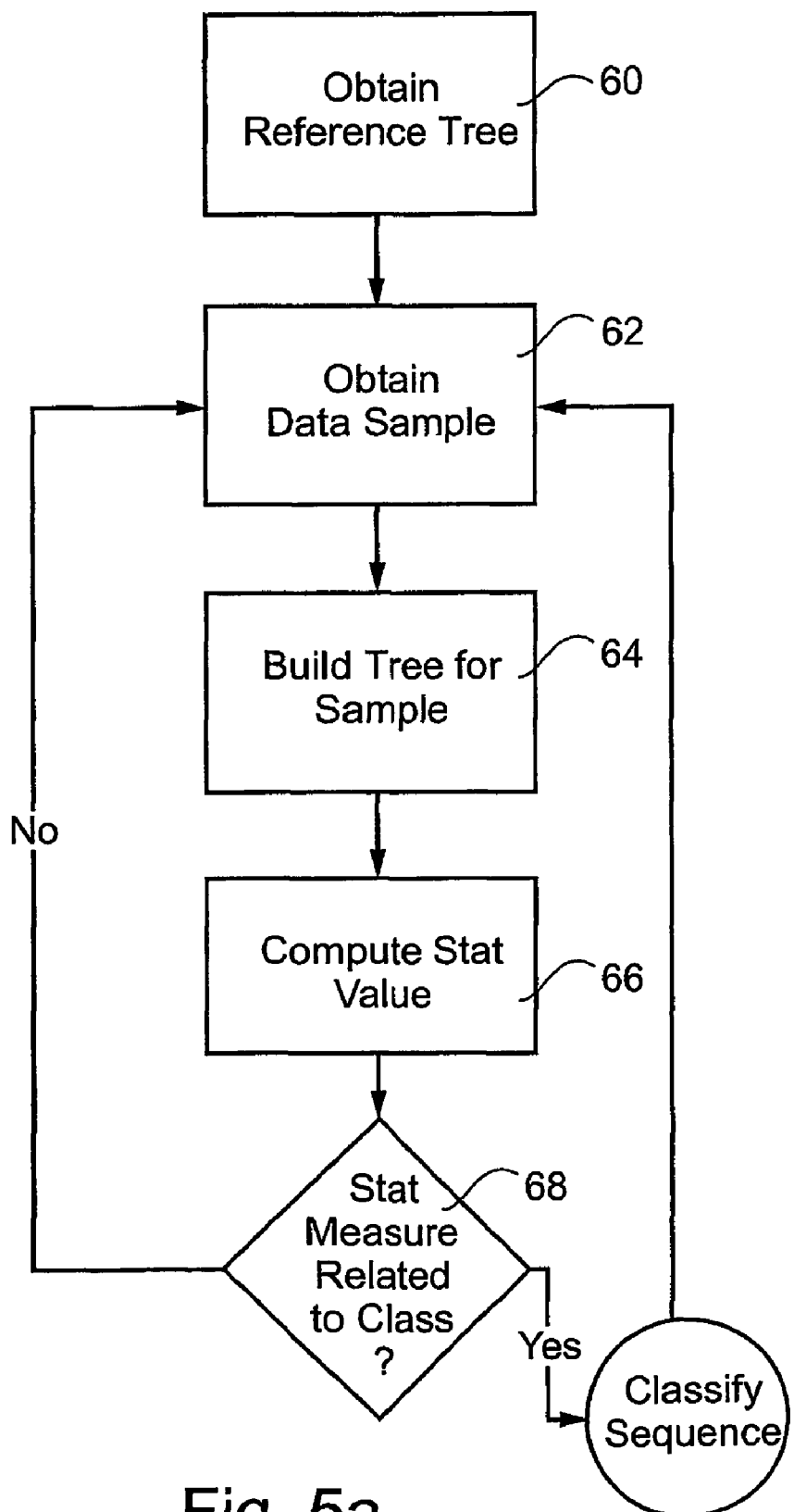
FIGS. 5a and 5b are simplified flow diagrams showing a process of monitoring using embodiments of the present invention.

Reference is now made to FIG. 5A, which is a simplified flow chart illustrating the control procedure used by the device of FIG. 2 to control a process or the like. In FIG. 5, a first stage 60 comprises obtaining a reference context-tree, $P_0(x,s)$. This may be done analytically or by employing the context algorithm to a long string of representative data, for example from a training set, or the model may be obtained from an external source.

In a second stage 62, a data source is monitored by obtaining data from the source. At succeeding points, a data sample is used to generate a current data tree $\hat{P}_i(x,s)$ from a sample of sequenced observations of size N. The sample size preferably complies with certain conditions that will be discussed in detail herein below. The sequences can be mutual-exclusive, or they can share some data points (often this is referred to as "sliding window" monitoring). The order of the sequence can be reorganize or permute in various ways to comply with time-dependent constraints or other type of side-information, which is available. Each sequence used to generate a model is referred to herein below as a "run" and contributes a monitoring point in the CSPC chart or a classification decision to CTC. Following the MDI principle referred to above, the structure of the current data tree is selected to correspond to the structure of the reference context-tree. Once the structure of the tree has been selected, then, in a model building stage 64, the counters of the current data context tree are updated using values of the string, and probability measures of the monitored context-tree are obtained, as will be explained in greater detail below.

Once the model has been built then it may be compared with the reference model, and thus the (log) likelihood ratio or the KL value can be calculated to give a distance between the two models in a step 66. As mentioned above, the log likelihood ratio is compared to a user predefined value. The KL value measures a relative distance between the current model and thus the monitored distributions $\hat{P}_i(x,s)$, and the reference distributions $\hat{P}_0(x,s)$ as defined in the reference model. In some cases it might be valuable to use several distance measures simultaneously and interpolate or average their outcomes.

Referring to the CTC the query step 68 indicates whether the obtain statistic value point to one of the classes. When considering the CSPC, the KL statistic value can plotted on a process control chart against process control limits in a query step 68. The control limits may for example comprise the upper control limit (UCL) given in equation (3.6) above. If the KL value is larger than the UCL it indicates that a significant change may have occurred in the process and preferably an alarm is set.

The process now returns to step 62 to obtain a new run of data, and the classifying process is repeated until the end of the process.

Considering FIG. 5A in greater detail, the data sample obtained at stage 62 may be considered as a sequence of observations $x^N = x_1, \ldots, x_N$, with elements $x_t$, $x_t = 1, \ldots, N$ defined over a finite symbol set, X, of size d. In stage 64, a primary output is a context tree $T_N$ for the sample, which context tree contains optimal contexts and the conditional probabilities of symbols given the optimal contexts. Namely, it is a model of the incoming data, incorporating patterns in the incoming data and allowing probabilities to be calculated of a likely next symbol given a current symbol.

Figure 5B:
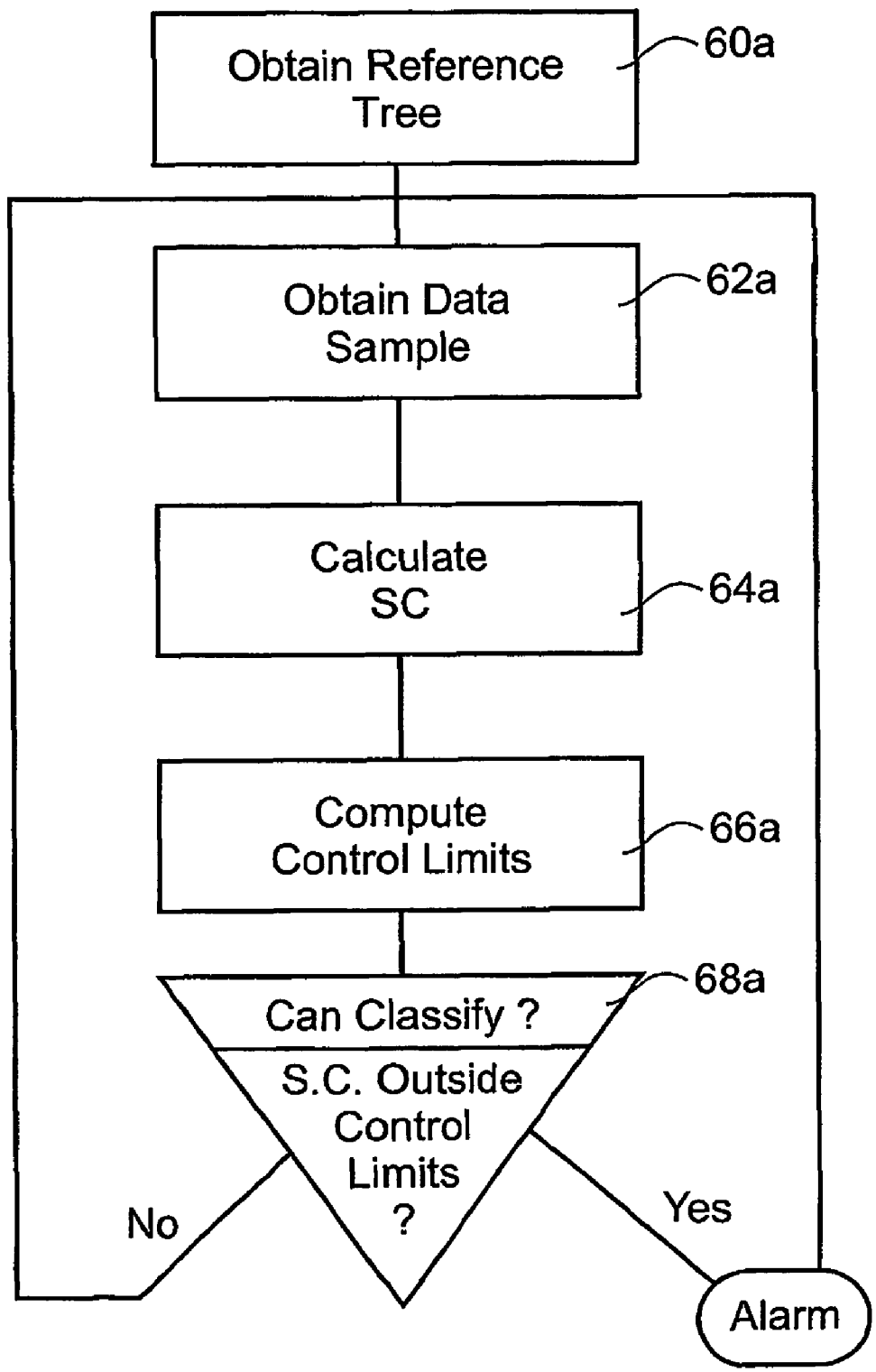

Reference is now made to FIG. 5B, which is a simplified flow chart showing how the same measurement may be carried out using stochastic complexity. A reference tree is initially obtained in step 60A. Then a data sample is obtained in step 62A. Stochastic complexity is calculated in step 64A and control limits are calculated in step 66A. Finally, the sample values are tested in step 68A to determine how to classify the sequence or whether the stochastic complexity is within the control limits.

Figure 6A:
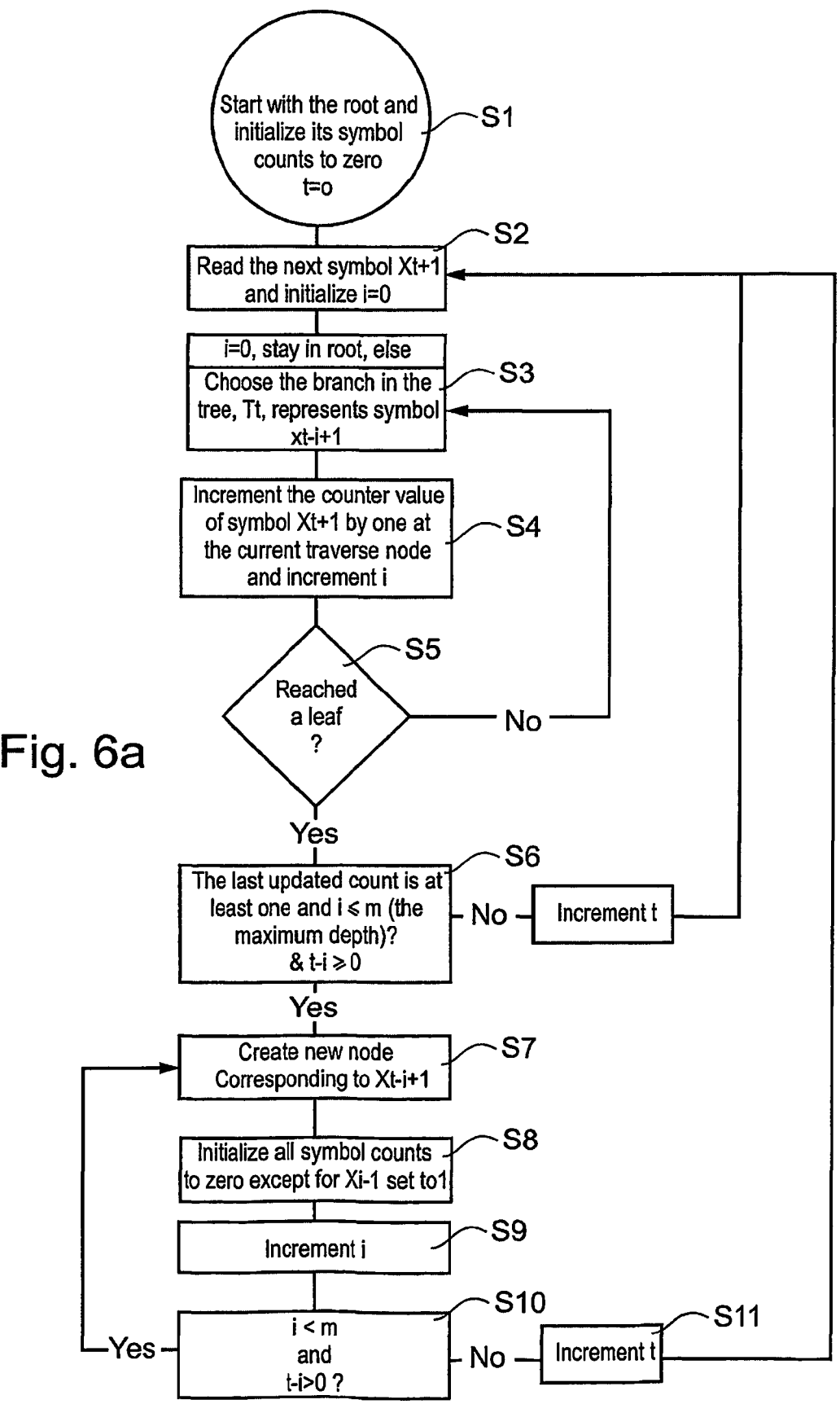
FIG. 6A is a flow diagram showing the procedure for building up nodes of a context tree according to a preferred embodiment of the present invention.

Reference is now made to FIG. 6A, which is a simplified flow chart showing an algorithm for carrying out stage 64 in FIG. 5, namely building of a context tree model based on the sample gathered in step 62. More specifically, FIG. 6A corresponds to stages 42 and 46, in FIG. 4. The tree growing algorithm of FIG. 6A constructs the tree according to the following rules (the algorithm depends on parameters that can be modified and optimized by the user):

A stage S1 takes a single root as the initial tree, $T_0$, and all symbol counts are set to zero. Likewise a symbol counter t is set to 0.

A stage S2 reads a $(t+1)^{th}$ symbol from the input sequence, thus, in the first iteration, $x_{t+1} = x_1$ is being read.

In stage S3 the algorithm begins a process of tracing back from a root node to the deepest node in the tree. If i=0 then tracing remains within the same root, otherwise the algorithm chooses the branch $T_t$ representing symbol $x_{t-i+1}$. Stage S4 is part of the traceback process of step S3. As each node in the tree is passed, the counter at that node, corresponding to the current symbol, is incremented by one.

In step S5, the process determines whether it has reached a leaf, i.e., a node with no descendents nodes. If so, the process continues with S6, otherwise it returns to S3.

S6 controls the creation of new nodes. S6 checks that the last updated counter is at least one and that further descendents nodes can be opened. It will, for example, detect a counter set to zero in step S8. Preferably, the last updated count is at least 1, i≦m(the maximum depth) and t−i≧0. Step S7 creates a new node corresponding to $x_{t-i+1}$. Step S8 generates one counter with value 1 and the other counters with zero value at new node creation. Those values may be detected by S6 when another symbol is read. Step S10 controls the retracing procedure needed to stimulate tree growth to its maximal size, by testing i≦m and t−1≧0 and branching accordingly.

Once a leaf has been reached in S5 or S10, then the traceback procedure is complete for the current symbol. The maximal allowed deepest node is set at an arbitrary limit (e.g. 5) to limit tree growth and size, and save computations and memory space. Without such a limit there would be a tendency to grow the tree to a point beyond which it is very likely to be pruned in any case.

Stage S6 thus checks whether the last updated count is at least one and if maximum depth has yet been reached. If the result of the check is true, then a new node is created in step S7, to which symbol counts are assigned, all being set in step S8 to zero except for that corresponding to the current symbol, which counter is set to 1. The above procedure is preferably repeated until a maximum depth is reached or a context $x_t x_{t-1} \ldots x_1$ is reached in stage S10. Thereafter the next symbol is considered in stage S2.

More specifically, having recursively constructed an initial tree $T_t$ from an initial symbol or string $x^t$, the algorithm moves ahead to consider the next symbol $x_{t+1}$. Then tracing back is carried out along a path defined by $x_t, x_{t-1}$, K and in each node visited along the path, the counter value of the symbol $X_{t+1}$ is incremented by 1 until the tree's current deepest node, say $x_t, \ldots, x_{t-l+1}$, is reached. Although not shown in FIGS. 6A and 6B, an initial string preceding $x^t$ may be used in order to account for initial conditions.

If the last updated count is at least 1, and l<m, where m is the maximum depth, the algorithm creates new nodes corresponding to $x_{t-r}$, 1<r≦m, as descendent nodes of the node defined in S6 The new node is assigned a full set of counters which are initialized to zero except for the one counter corresponding to the current symbol $x_{t+1}$, which is set to 1. Retracing is continued until the entire past symbol history of the current input string has been mapped to a path for the current symbol $x_{t+1}$ or until m is reached. r being the depth of the new deepest node, reached for the current path, after completing stage S7.

Figure 6B:
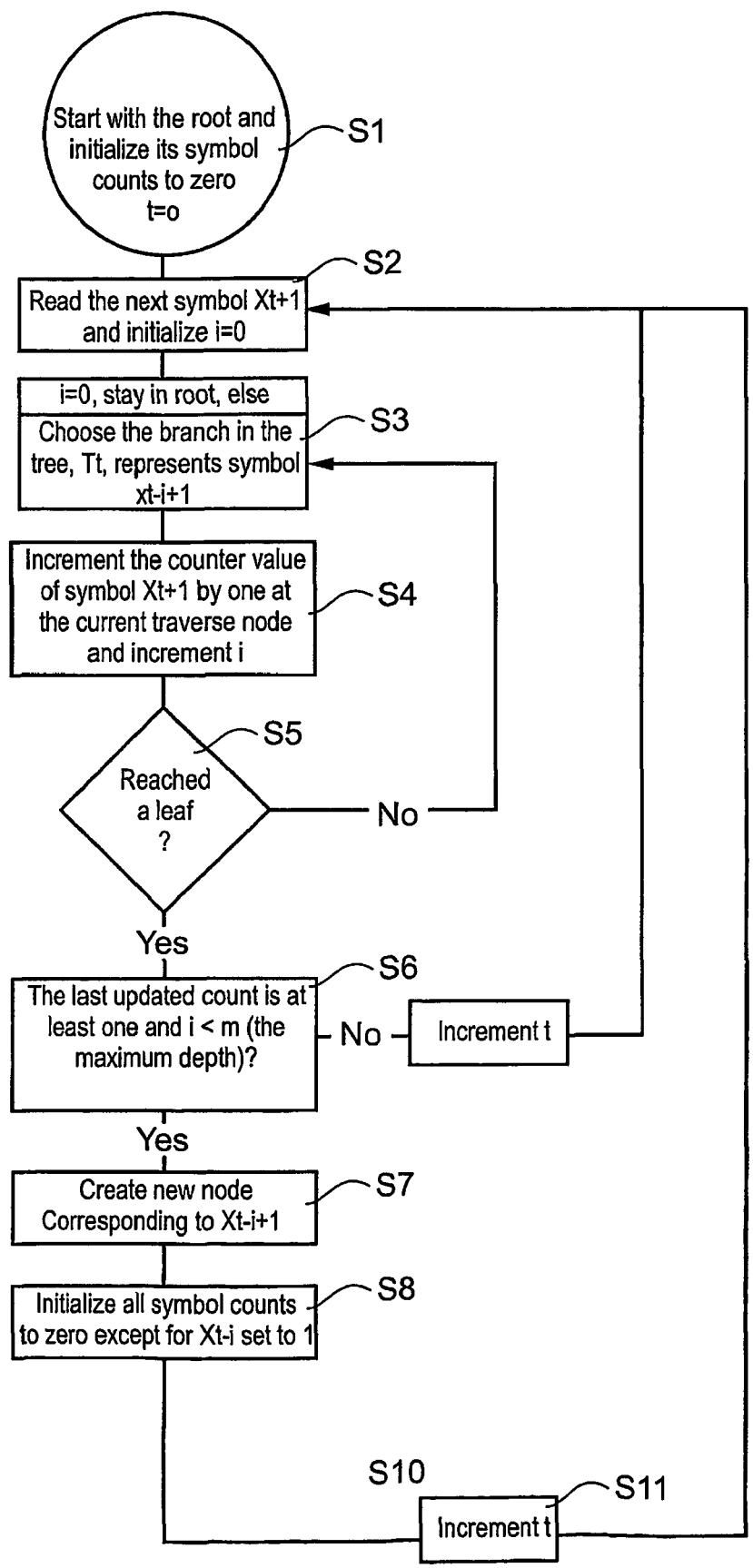
FIG. 6B is a variation of the flow chart of FIG. 6A which carries out tree growth to reach a predetermined depth faster.

Reference is now made to FIG. 6B, which is a simplified flow chart showing a variation of the method of FIG. 6A. Steps that are the same as those in FIG. 6A are given the same reference numerals and are not referred to again except as necessary for understanding the present embodiment.

In FIG. 6B, the steps S9 and S10 are removed, and step S8 is followed directly by step S11, thereby to reduce the computational complexity. While the previous algorithm is more accurate, in this algorithm, the tree grows slowly—at most one new node per symbol. Thus in the beginning—when the tree has not yet grown to its maximal depth—some counts are lost. If the sequence length is much longer compared to the maximal tree depth, than the difference in the counter values produced by both algorithms will be practically insignificant for the nodes left after the pruning process.

In order to understand better the algorithms of FIG. 6, reference is now made to FIGS. 7-9 which are diagrams of a model being constructed using the algorithm of FIG. 6. Further illustrations are given in Tables A1 and A2.

In FIGS. 7-9, tree 100 initially comprises a root node 102 and three symbol nodes 104-108. Each one of nodes 102-108 has three counters, one for each of the possible symbols "a", "b" and "c". The counters at the root node give the numbers of appearance of the respective symbols and the counters at the subsequent, or descendent, nodes represent the numbers of appearances of the respective symbol following the symbol path represented by the node itself. Thus the node 104 represents the symbol path "a". The second counter therein represents the symbol "b". The counter being set to 1 means that in the received string so far the number of "b"s following an "a" is 1. Node 106 represents the symbol path "b" and the first counter represents the symbol "a". Thus the first counter being set to "1" means that in the received string so far the symbol "a" has appeared once following a "b". The second counter being on "0" implies that there are no "b"s followed by "b"s.

Node 108 represents context "b a" corresponding to the symbol path or the sequence "a b" (recall that contexts are written in reverse order). The first counter, representing "a" being set to "1" shows that there is one instance of the sequence "a b" being followed by "a".

In FIG. 8, a fourth symbol $x_4$=b is received. The steps S3 to S10 of FIG. 6 are now carried out. The symbol b, as preceded by "a b a" in that order can be traced back from node 104 to 102, (because the traceback covers the "b a" suffix of the sequence). The "b" counters are incremented at each mode passed in the traceback. Likewise the sequence "a b a" can be traced back from node 108 to the root, again incrementing the "b" counters each time.

In FIG. 9, a new node 110 is added after node 104, representing step S7 of FIG. 6. The node is assigned three counters as with all previous nodes. The "b" counter thereof is set to 1 and all other counters are set to "0" as specified in step S8 of FIG. 6. It is noted that the context for the new node is "a b", thus, representing the sequence "b a".

Returning now to the tree pruning stage 46 of FIG. 4, it is necessary to prune the tree, as will be described below, to obtain what may be referred to as the optimal contexts of TN. Tree pruning is achieved by retaining the deepest nodes w in the tree that practically satisfy equation 2.3 above. The following two pruning rules apply:

Pruning rule 1: the depth of node w denoted by |w| is bounded by a logarithmic ratio between the length of the string and the number of symbol types, i.e., |w|≦log(t+1)/log(d); and, Pruning rule 2: the information obtained from the descendant nodes, sb ∀b∈X, compared to the information obtained from the parent node s, is larger than a 'penalty' cost for growing the tree (i.e., of adding a node).

The driving principle is to prune any descendant node having a distribution of counter values similar to that of the parent node. In particular, we calculate $\Delta_N(sb)$, a measure of the (ideal) code-length-difference of the descendant node sb, ∀b∈X, $$\Delta_N(sb) = \sum_{x \in X} n(x \mid sb) \log\left(\frac{\hat{P}(x \mid sb)}{\hat{P}(x \mid s)}\right) \quad (4.1)$$

and then require that $\Delta_N(w) \geqq C(d+1)\log(t+1)$, wherein logarithms are taken to base 2; and C is a pruning constant tuned to process requirements (with default C=2.

The tree pruning process is extended to the root node with condition $\Delta_N(x^0)=\infty$, which condition implies that the root node itself cannot be pruned.

Figure 10:
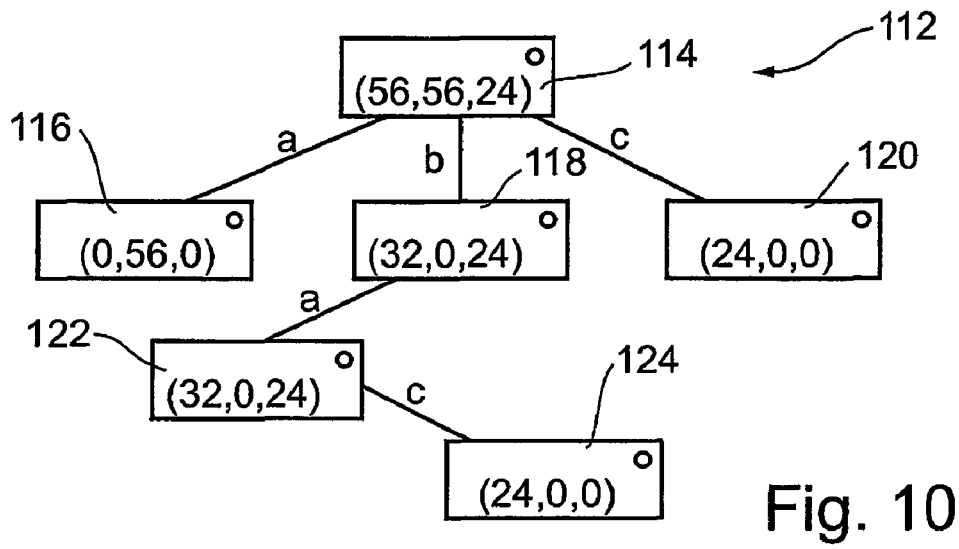

Reference is now made to FIG. 10, which is a simplified diagram showing a pruned counter context-tree 112 constructed by applying the tree building of FIG. 6 followed by tree pruning on a string containing 136 symbols—eight replications of the sub string: (a, b, a, b, c, a, b, a, b, c, a, b, a, b, a, b, c). The tree comprises a root node 114 and five further nodes 116-124. By contrast, the unpruned tree, from which this was taken, may typically have had three decsendent nodes for each node Returning again to FIG. 4, and stage 48, selection of optimal contexts, is now described in greater detail. In stage 48, a set of optimal contexts, Γ, containing the S shortest contexts satisfying equation 2.3 is specified. An optimal context can be either a path to a leaf (a leaf being a node with no descendants) or a partial leaf in the tree. A partial leaf is defined for an incomplete tree as a node, which is not a leaf. Now, for certain symbol(s) the path defines an optimal context satisfying equation 2.3, while for other symbols equation 2.3 is not satisfied and a descendant node(s) is created. The set of optimal contexts is specified by applying the following rule:

$$\Gamma = \left\{ s : \sum_{x \in X} \left( n(x \mid s) - \sum_{b \in X} n(x \mid sb) \right) > \varepsilon \right\} \forall s \in T_t, \quad (4.2)$$

where ω=0 is the default value of a user-defined parameter. This means that Γ contains only those contexts that are not part of longer contexts. When the inequality in expression 4.2 turns into equality, that context is fully contained in a longer context and, thus, is not included in F. It is noted that in each level in the tree there is a context that does not belong to a longer context and, therefore, does not satisfy equation 4.2. This is generally due to initializing conditions. Such inconsistency can be solved by introducing an initiating symbol string.

In summary, Γ contains all the leaves in the tree as well as partial leaves satisfying equation 4.2 for certain symbols.

Returning to FIG. 10, and node 122 corresponds to string history or context s=ba and is, as defined above, a partial leaf (acts as an optimal context) for symbols a and c. This is firstly because the longer context s=bac does not include all symbol occurrences of symbols a and c. Secondly, the contexts bab and baa were pruned and lumped into the context ba. Applying equation 4.2 to the pruned counter context-tree presented in FIG. 10 results in four optimal contexts Γ={a; bac; c; ba}. The first three contexts in Γ are leaves, the latter is a partial leaf and defines an optimal context for symbols a and c. Considering now in greater detail stage 50, estimation of parameters in FIG. 4, the estimation stage is composed of three steps as follows:

1) the probabilities of optimal contexts are estimated and denoted by P̂(s), s∈Γ;
2) the conditional probabilities of symbols given the optimal contexts are estimated and denoted by P̂(x|s), x∈X, s∈Γ; and
3) the estimated joint probabilities of symbols and optimal contexts are calculated P̂(x, s), x∈X, s∈Γ.

Given the set of optimal contexts and the pruned counter tree, the probability of optimal contexts in the tree, P̂(s), s∈Γ, are estimated by their frequency in the string:

$$\hat{P}(s) = \frac{n(s)}{\sum_{s \in \Gamma} n(s)} = \frac{\sum_{x \in X} \left( n(x \mid s) - \sum_{b \in X} n(x \mid sb) \right)}{\sum_{s \in \Gamma} \sum_{x \in X} \left( n(x \mid s) - \sum_{b \in X} n(x \mid sb) \right)} \quad \forall x \in X, s \in \Gamma$$

where n(s) is the sum of the symbol counters in the corresponding leaves (or partial leaves) that belong to the optimal context s and not to a longer context sb b∈X. Each symbol in the string thus belongs to one out of S disjoint optimal contexts, each of which contains n(s) symbols. An allocation of symbols of a sufficiently long string to distinctive optimal contexts can be approximated by the multinomial distribution.

Returning to FIG. 10, and the estimated probabilities of optimal contexts in FIG. 6 are given respectively by, {P̂(a), P̂(bac), P̂(c), P̂(ba)}={56/136, 24/136, 24/136, 32/136}.

Once the symbols in the string are partitioned to S substrings of optimal contexts, the conditional probabilities of symbol types given an optimal context are estimated by their frequencies in the respective substring, $$\hat{P}(x \mid s) = \frac{n(x \mid s) - \sum_{b \in X} n(x \mid sb)}{n(s)} \quad \forall x, b \in X, s \in \Gamma \quad (4.3)$$

where $$\frac{0}{0} \equiv 0.$$

The distribution of symbol types in a given optimal context is, thus, approximated by another multinomial distribution.

An alternative predictive approach to equation 4.3 was suggested. It is implemented in cases where one needs to assign strictly positive probability values to outcomes that may not actually have appeared in the sample string, yet can occur in reality. Thus, 17 P̂(x|s)=n(x|s)+12×Xn(x|s)+d2×X, s(4.4)

The choice among the two alternative procedures above depends both on the knowledge regarding the system states and on the length of the string used to construct the context-tree. The latter approach is suitable for applications involving forecasting.

Figure 11:
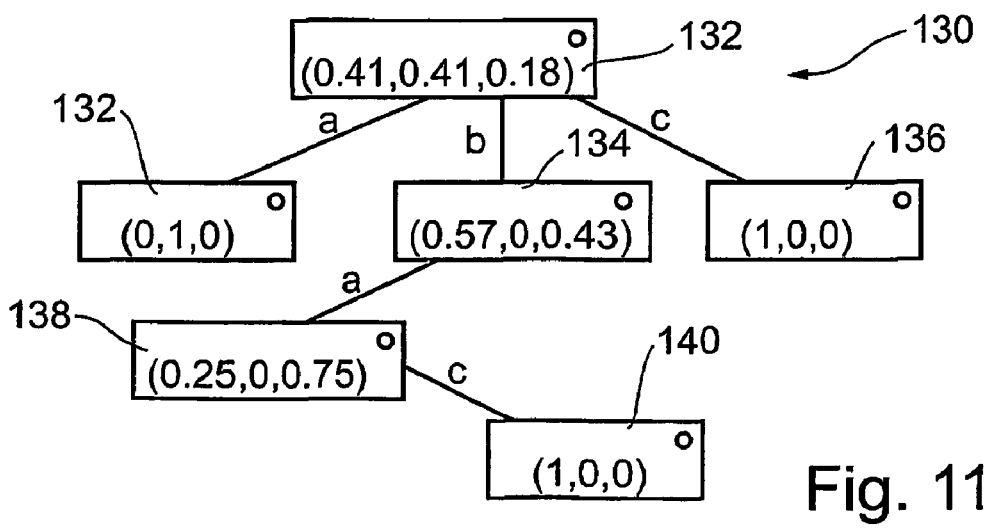
Figure 17:
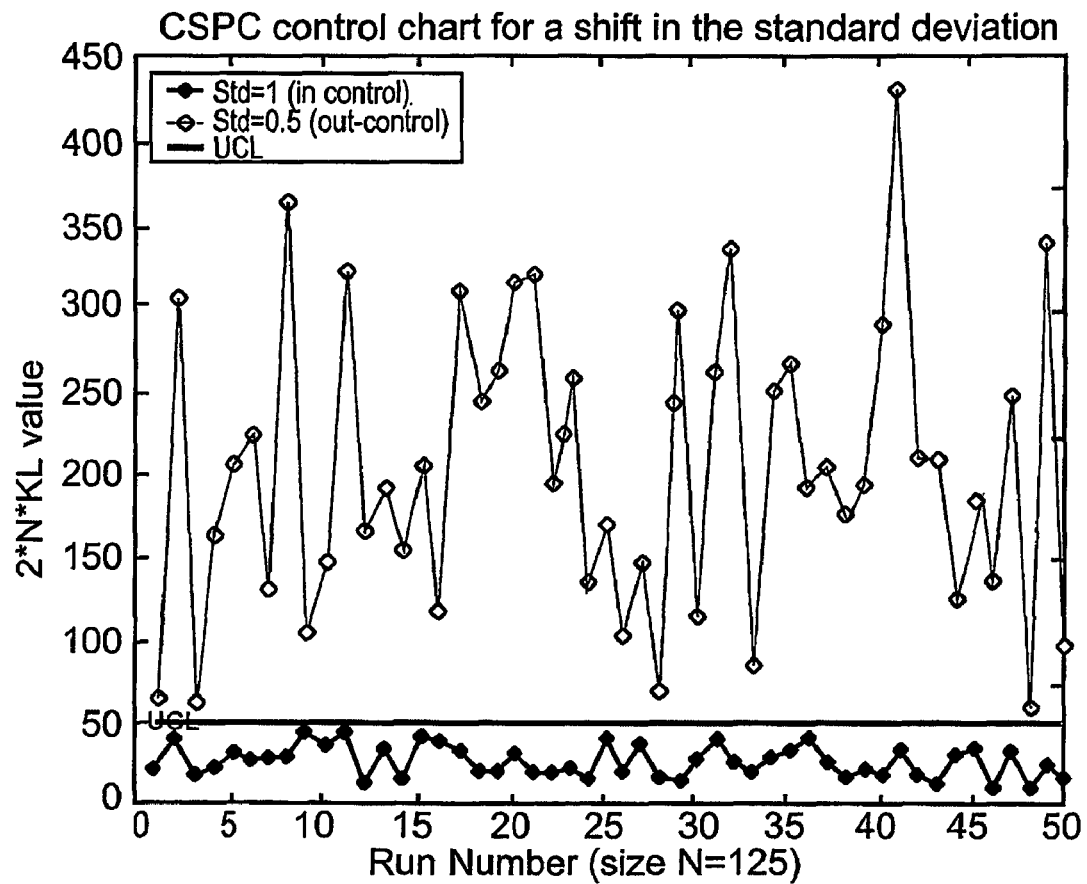
Figure 18:
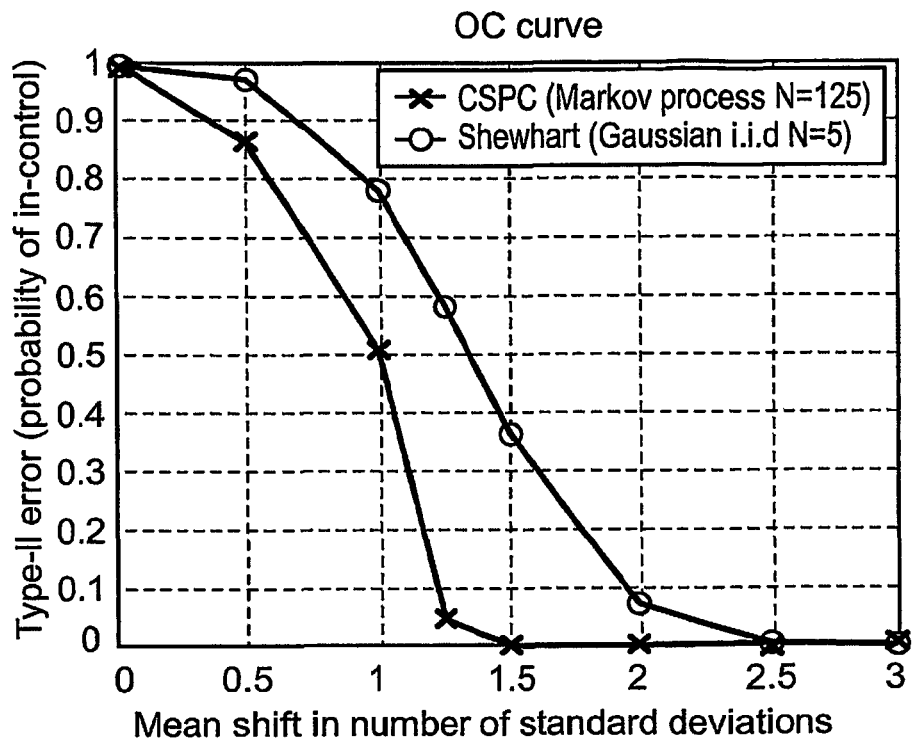
Figure 19:
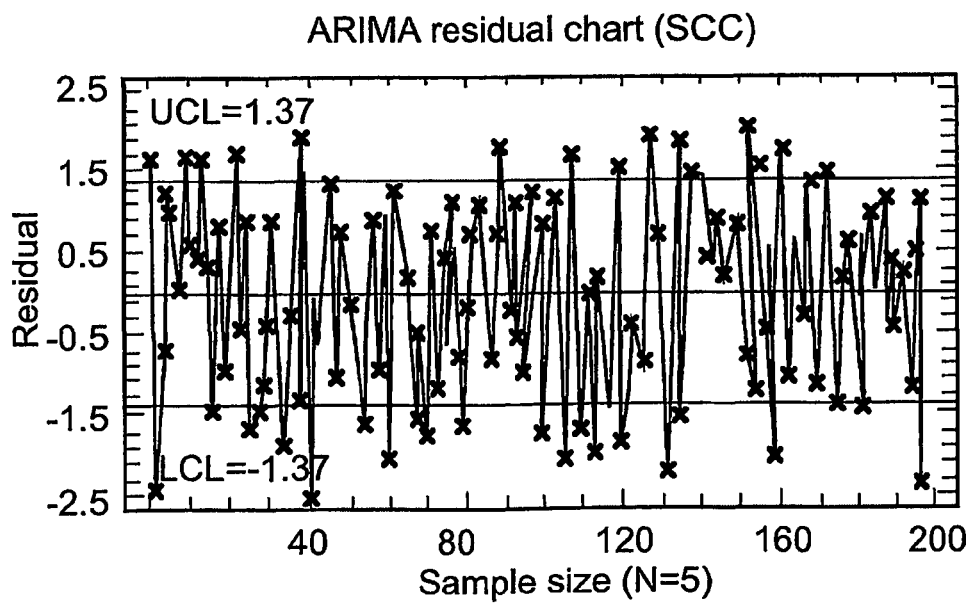
Figure 20:
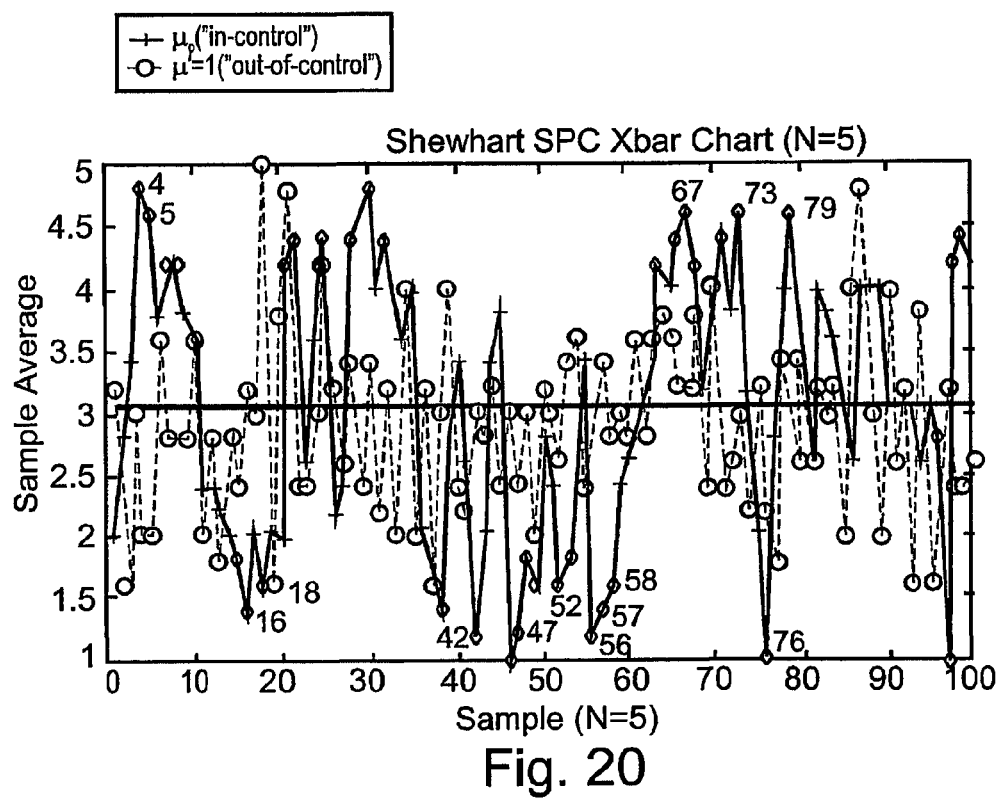
Figure 21:
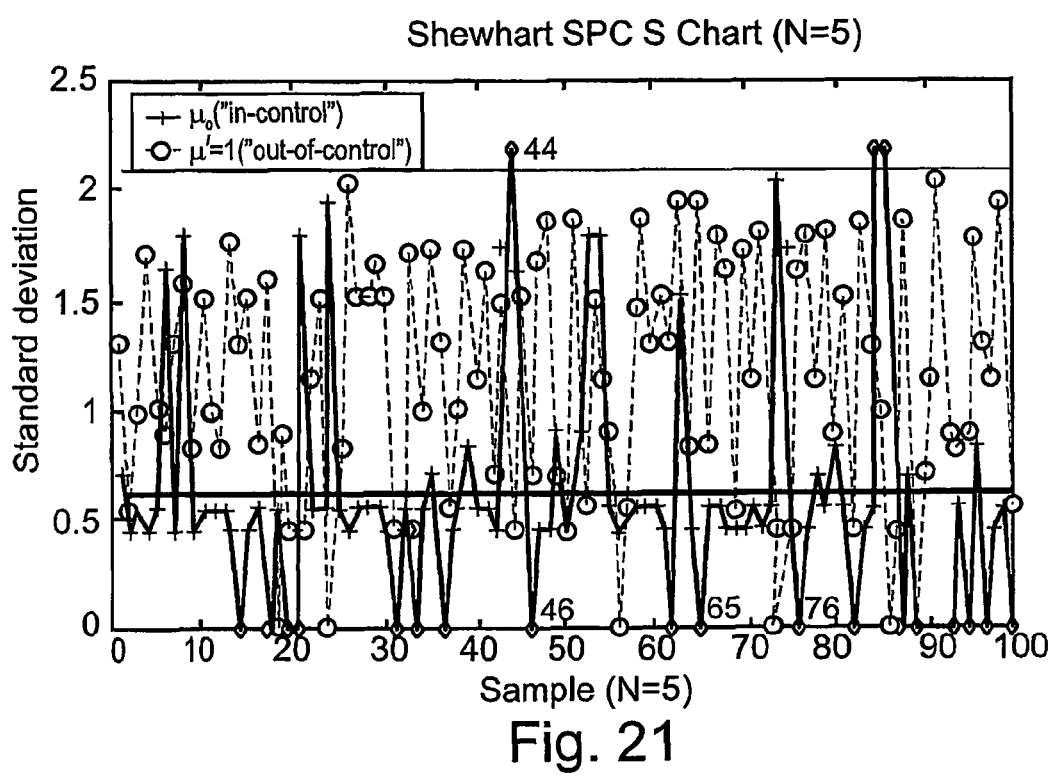
Figure 22:
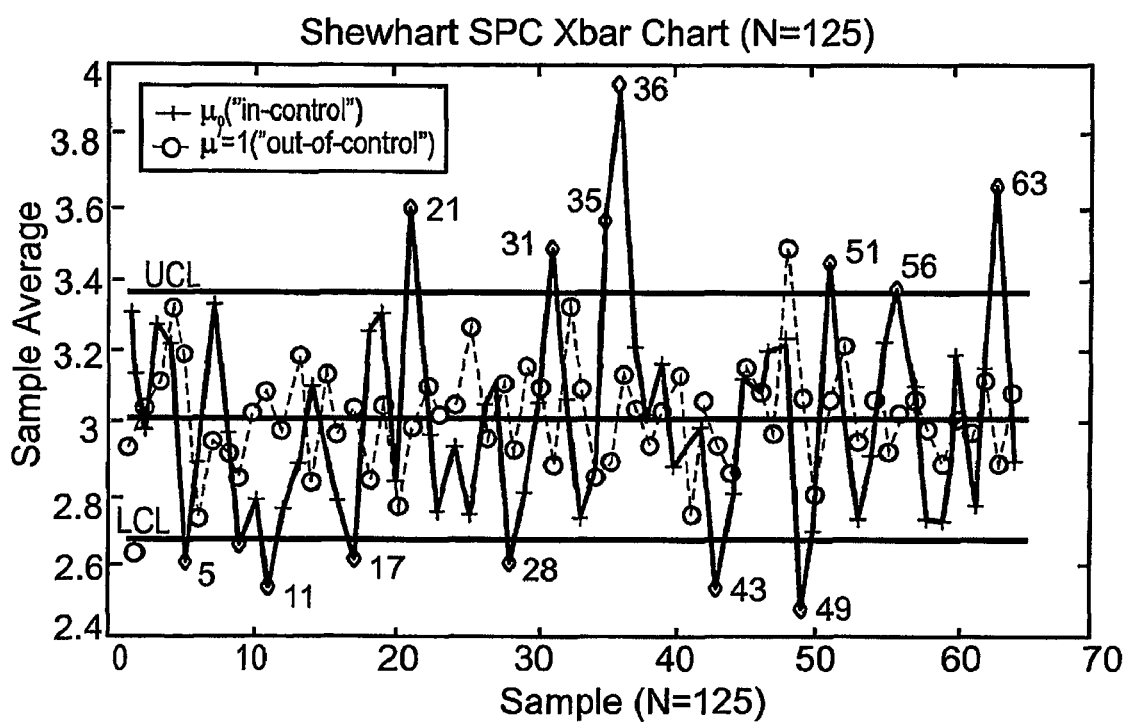
Figure 23:
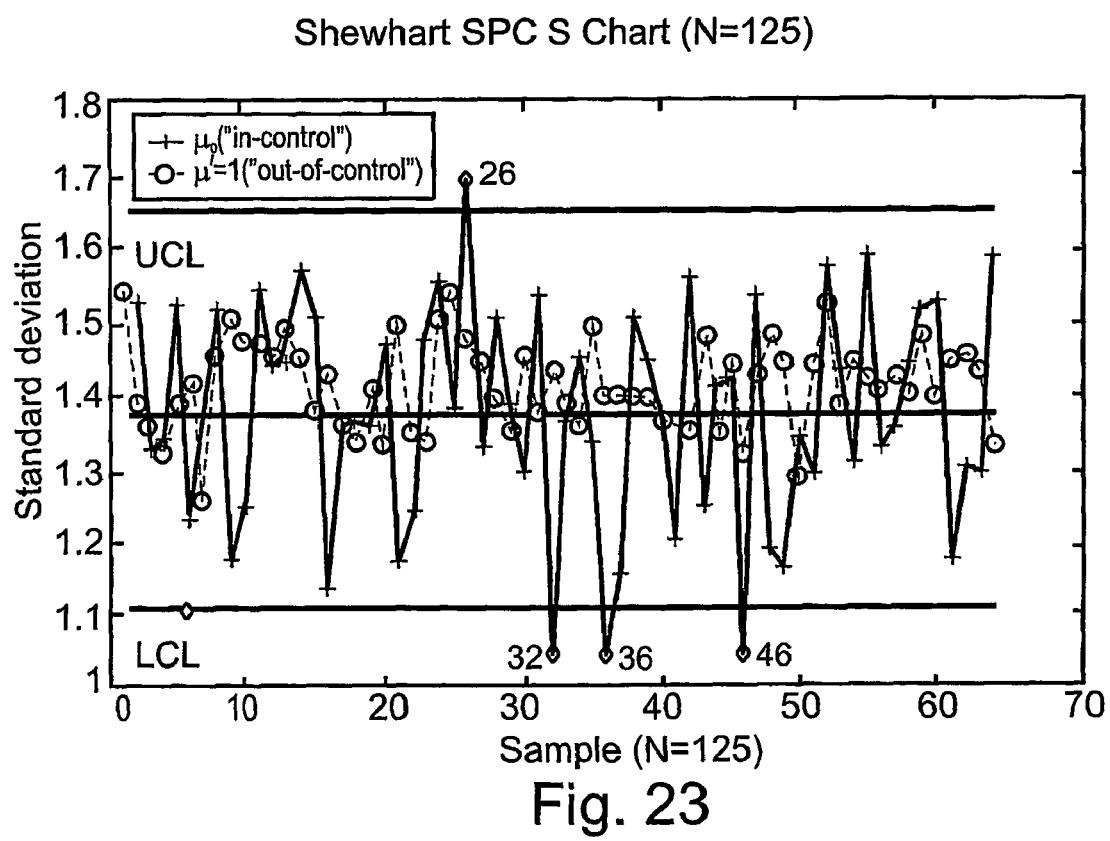

Reference is now made to FIG. 11, which is a simplified tree diagram showing a tree 130 having a root node 132 and five other nodes 134-140. The counters now contain probabilities, in this case the estimated conditional probabilities of symbols given contexts. The probability estimates are generated by applying equation 4.3 to the counter context-tree 112 of FIG. 11. For example, the conditional probability of a symbol type x∈{a, b, c} given the context s=a, is estimated as P̂(x|a)=(0,56/56,0)=(0,1,0), whereas the conditional probabilities of a symbol x∈{a,b,c} given the context s=ba is estimated as P̂(x|ba)=(8/32,0,24/32)=(0.25,0,0.75). The probabilities of symbols in non-optimal contexts are also shown for general information.

As shown in the figure the optimal contexts are {132,140, 136,138}.

Returning now to FIG. 3a tree 30 is the context tree generated from a string of length N=1088 (64 replications of the basic string a, b, a, b, c, a, b, a, b, c, a, b, a, b, a, b, c). The maximum tree depth has increased from three to five levels, as opposed to the preceding examples. Nevertheless, the number of optimal contexts acting as states has only increased from four to five. It is pointed out that had a Markov chain model of order k=5 been used, it would have been necessary to estimate transition probabilities between $3^5$=243 states, most of which are redundant in any case.

The joint probabilities of symbols and optimal contexts that represent the context-tree in its final form are evaluated thus:

$\hat{P}(x,s) = \hat{P}(x|s) \cdot \hat{P}(s), x \in X, s \in \Gamma.$

As explained above with respect to FIG. 5, the model as built in accordance with the procedures outlined in FIGS. 6-11 can be used in the comparison stage of FIG. 5 to obtain information about the comparative statistical properties of data sequences.

The above procedure is summarized and illustrated in the following two tables for string $x^6$=4, 4, 4, 3, 3, 2 where d=5, X={0, 1, 2, 3, 4}:

TABLE A1

Tree growing and counter updating stage in context algorithm for string $x^6$ = 4,4,4,3,3,2

| Steps | Tree | Description |
| --- | --- | --- |
| Step 0: $T_0$ |  | Initialization: the root node, λ, denotes the empty context |
| Step 1: $T_1$ $x^1$ = 4 |  | The only context for the first symbol is λ, the counter n(x = 4\|λ) was incremented by one. |
| Step 2: $T_2$ $x^2$ = 4, 4 | 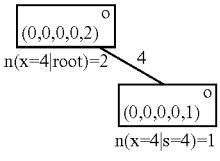 | The counters n(x = 4\|λ) and n(x = 4\|s = 4) are incremented by one. The node of the context s = 4 is added to accumulate the counts of symbols given the context s = 4. |
| Step 3: $T_3$ $x^3$ = 4, 4, 4, | 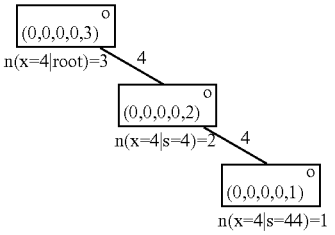 | The counter of the symbol 4 is incremented by one in the nodes from the root to the deepest node along the path defined by the past observations. In this case, the counters - n(x = 4\|λ) and n(x = 4\|s = 4) are incremented by 1. A new node is added for the context s = 44. And n(x = 4\|s = 44) = 1. |
| Stage 4: $T_4$ $x^4$ = 4, 4, 4, 3 | 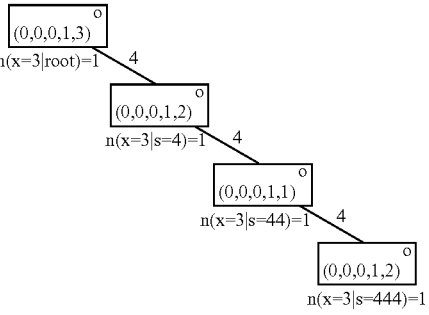 | The counters - n(x = 4\|λ), n(x = 4\|s = 4) and n(x = 4\|s = 44) are incremented by one since the past contexts are s = λ, s = 4, s = 44. A new node is added for the context s = 444 of the observation $x_4$ = 3. |
| Stage 5: $x^5$ = ..., 4, 3, 3, | 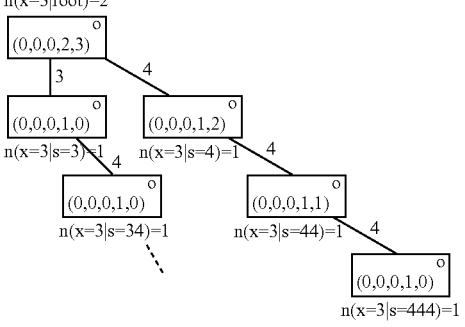 | Add new nodes for the contexts s = 3, s = 34, s = 344 . . . . Update the counter of the symbol x = 3 from the root to the deepest node on the path of past observations. |

TABLE A1-continued

Tree growing and counter updating stage in context algorithm for string $x^6 = 4,4,4,3,3,2$

| Steps | Tree | Description |
|---|---|---|
| Stage 6: $x^6 = \ldots,$ 3, 3, 2 | [Tree diagram: root n(x=2\|root)=1 (0,0,1,2,3) with branches 3 and 4; branch 3 → (0,0,2,1,0) with sub-branches 3 → (0,0,0,1,0) n(x=2\|s=33)=1 and 4 → (0,0,0,1,0) n(x=3\|s=34)=1; branch 4 → (0,0,0,1,2) with branch 4 → (0,0,0,1,1) with branch 4 → (0,0,0,1,0) n(x=3\|s=444)=1] | Update the counter of the symbol x = 2 from the root to the deepest node on the path of past observations. Add the contexts: s = 33 and so on. |

TABLE A2

Pruning stage in context algorithm for the string $x^6 = 4,4,4,3,3,2$

| Rule | Tree | Description |
|---|---|---|
| Rule 1: | [Tree: (0,0,1,2,3) with branches 3 → (0,0,1,1,0) and 4 → (0,0,0,1,2)] | Rule 1: Maximum tree Depth $\leq \log(t)/\log(d) = \log(6)/\log(5) = 1.11$ The maximum tree depth is of level one. Thus, all nodes of level 2 and below are trimmed. |
| Rule 2: | [Tree: (0,0,1,2,3)] | Rule 2: for the rest of the nodes in level one and the root, we apply trimming rule 2. The threshold for C = 2 is: $\Delta_6(u) > 2(d + 1)\log(t + 1) = 33.7$ And for each of the nodes: $\Delta_6(sb = \lambda 3) = 0 + 0 + 1 \cdot \log\left(\dfrac{0.5}{1/6}\right) + 1 \cdot \log\left(\dfrac{0.5}{2/6}\right) + 0 = 2.17$ $\Delta_6(sb = \lambda 4) = 0 + 0 + 0 + 1 \cdot \log\left(\dfrac{1/3}{2/6}\right) + 2 \cdot \log\left(\dfrac{2/3}{3/6}\right) = 0.83$ The code-length difference is below the threshold, hence the first level nodes are trimmed. |

Tuning of the Model for Specific Conditions

The use of context trees as modelers for analysis and pattern recognition, in particular for biological data sets, may be modified in various ways to improve performance. It is noted that the various parameters of context tree model can be used to optimize performance for different pattern recognition problems, by using side information specific to the problem, and by using empirical and numerical tests. The flexibility of the modelers is too large to be indicated fully here. Nevertheless, in the following list several optional modifications of the model parameters are indicated for specific experimental conditions:

Combination of several separate context tree models: several fixed string length models are tuned together. That is to say each model is tuned on a different part of a long input string, through manipulation of the context tree algorithm with limited size buffers and with jumping over irrelevant string segments. Then, instead of using a given string length, the string is divided into segments and each segment is handled by a different context tree model. For example, in the E-coli promoter-recognition problem, it is known that most promoters have two different recognition sites, each having six base-pairs (bp) and separated by an intermediate segment of variable length. Therefore, one can modify the input string length for training and identification.

For a model based on a string length of 12 bp (and without implementing other optimization procedures—such as non-homogeneous trees), a context tree was experimentally identified that yielded a True Positives value of 69.75% and a True Negatives value of 67.94% using a cross-validation set. Then by using the same non-optimized model which is based on two separated context trees, each of which was for input strings of 6 bp, the results improved to a True Positives value of 71.43% and a True Negatives value of 72.01% for the cross-validation set. Optimizing the other parameters of the tree model, enabled a dramatic improvement to yield a True Positives value of 92.86% and a True Negatives value of 91.5%. The same idea may be extended to using a model which is based on four different context trees for input strings of 3 bp each. Such partitions increase the position-dependant sensitivity of the model, however it leads to some loss of information regarding the dependence of border regions between the partial sequences. An optimization procedure, thus, may be performed for finding the optimal split in terms of the recognition efficiency.

Sliding Windows: the division of an input string into substrings can be performed either to obtain mutual exclusive sub-strings, that do not share common sequences, or in the manner of a sliding-window, that is to say forming substrings from incremental lengths along the sequence. For example, in the problem of identification of DNA coding regions, at each step an input string of a fixed length contains several new bp in comparison to the input string of the last step. In this manner, the model is gradually modified and the classification can be indicated in earlier stages.

Non-Homogeneous models: in non-homogenous models, different alternating context tree models are interlaced in a predetermined sequence that can capture cyclic phenomena in the string. For example, in the coding, non-coding classification problem, it is known that coding DNA segments have an internal structure of triplets (or codons) and the position in the triplet is important for correct classification. It is possible to grow three different context trees—one for each one of the relative positions of the basis acids in the codon—and when handling large strings of coding, or suspected coding DNA, the predictions of the three trees are interlaced together and generate the prediction of the DNA segment.

To illustrate the above, an experiment was carried out using a benchmark dataset, for accuracy discrimination between coding and non-coding DNA segments of length 54/108/162 bp respectively. Accuracies of 85.0/90.5/92.6 respectively were obtained using the non-homogenous method compared to accuracies of 74.3/77.5/80.5 using only one context tree. The non-homogenous results are better than the previously best results on the dataset using other non-homogenous methods: 80.7/84.9/88.0. That is to say the present method provided an approximate 4% improvement.

Predictive vs. Non Predictive models: Predictive models assign non-zero probabilities to events that were never observed in the training set, while non-predictive models assign zero probability to events that were never observed in the training set. The choice of the appropriate model is based on the feasibility of the un-observed events: if unobserved events are not feasible, than the non-predictive formula is more accurate. Once again, the use of predictive vs non predictive models can be checked against cross-validation properties.

Selection of the tree truncation threshold: the threshold is one of the most important default parameters and directly determines the size of the final model. Indirectly it determines the computational aspects of the algorithm, and the accuracy of the model. It may be optimized for each application. For example, in predictive applications such as time series forecasting it was empirically found that a smaller than default threshold improves the quality of the prediction.

Tree Construction Parameter: The tree construction parameters proposed in the algorithm are default parameters for optimization. Such parameters include: i) the tree maximum depth; ii) the algorithm buffer size; iii) value of pruning constants; iv) the length of input sequences; v) the order of input symbols; vi) the number of nodes to grow after a leaf is reached; vii) other parameters indicated in FIG. 6A etc. Further improvement of the model is possible by optimization of the default parameters in accordance with the conditions of each specific application.

In general the Markov model does not take into account the possibility of position dependence in the model nor the possibility of varying order, partial leafs. The stochastic models discussed herein do take such position information into account.

APPLICATIONS

Use of the above context model to monitor changes in state has a wide range of applications. In general the model part may be applied to any process which can be described by different arrangements of a finite group of symbols and wherein the relationship between the symbols can be given a statistical expression, although, in the present disclosure, emphasis is placed on spatially related data. For example—sequences of nucleotides belonging to an alphabet symbol set of four letters, or a sequence of amino acids belonging to an alphabet set of 20 letters, or a sequence of proteins structures described by an alphabet set letters for primary secondary and 3D structure—all make good candidates for consideration. The comparison stage as described above allows for changes in the statistics of the symbol relationships to be monitored and thus modeling plus comparison may be applicable to any such process in which dynamic changes in those statistics are meaningful.

In the field of biology an important application concerns the recognition and prediction common function amongst biological sequences, for example within promoters and coding sequences from amongst DNA sequences, or in the recognition or prediction of three-dimensional shape and function in proteins. DNA sequences are sequences of four bases termed Adenine, A, Cytosine, C, Guanine, G, and Thiamine, T, and combinations of the four bases provide both acting regulatory sequences, encoding sequences for amino-acids to be used in proteins, intron sequences which are transcribed yet not translated and and non-coding sequences of yet unidentified function, including high, moderate and low repetitive have a certain similarity in the statistical distribution of the bases, however, such similarity is not at all trivial for detection.

In general, any kind of biological sequence can be analyzed in the above way to identify or predict properties. Provided groups of sequences can be identified that share a common functionality or structure, they may be used as a training data base to construct a tree model and later identify whether a new sequence belongs to that group or has a similar feature or structure that might apply a certain relation to that group.

Thus, for example, promoters that form a certain group of DNA sequences that share a common functionality can be used as a training data base to construct a tree and later identify whether a new sequence belongs to that group.

NUMERICAL EXAMPLE

By way of example, an experimental attempt to identify promoter regions in *E. coli* DNA was described in FIG. 3b. An input string of observations is introduced to a feature transformation module along with a context-tree model. The tree model is constructed by the methods described above based on a training set generated by concatenating several 12 base-pairs sequences of known promoters. The context-tree model represents the probabilistic structure in the training set but with a huge reduction of dimensionality. Instead of representing all conditional statistics that emerged from the training set, the tree represents only those statistics that were found to be significant. The transformation computes the log-likelihood of the input string being a "promoter" or a "non-promoter" according to the tree structure (i.e., the feature vector, y). The log-likelihood values are then introduced to the classifier, which decides based on a given threshold whether to classify this input string as a promoter or not.

More specifically, in the experiment, 238 DNA sequences taken from E-Coli promoters (2 six mers) were coded by a numerical alphabet (explain A=1, C=2, G=3, T=4) and arranged into a long source string S. A context tree modeler was set to build a tree from the data using a context length and deepest node, of 5, that is to say, at each stage of building of the tree only the five previous symbols were retained and a buffer having symbol length 12 was set. Preferably, the buffer length serves to reset the process of growing the context tree.

In the experiment a training set of 238 E-Coli promoter sequences were available. In a first experiment—performed without cross validation—all the training set was used to built a tree model and then the model was used to specify the likelihood for each promoter—i.e., the promoter itself was also part of the training set. In the second experiment 238 different training sets were used to calculate the likelihood of each promoter—each training set containing 237 promoters, i.e., without the promoter itself.

In the cross-validation experiment, reference context trees were built in each case for sequences of 237 promoters and then an attempt was made to identify the $238^{th}$ promoter from the source string S.

The above experiment is referred to as a cross-validation experiment, and its purpose is to test the quality of a model built with 237 promoters on promoter No. 238 which did not take part in the tree growing process.

The result achieved was that the third context tree in each case, namely that built from a concatenation of three replicas of the string S, gave correct identification of the 238th string in 75% of cases—without optimizing the tree parameters at all, thus providing an illustrative example. In a later experiment, by optimizing certain tree parameters, the accuracy level was raised to 94%.

The first experiment was repeated with position dependence and with sub trees and improvements were obtained. Thus, in the sub trees experiment each promoter was presented by two separate 6 base pairs trees instead of one 12 base pair tree. The reason is that the E Coli promoter is composed of two 6 bp sites that are separated by several nucleotides. When calculating the likelihood of a promoter, the first 6 bp was calculated using the first tree model and the second 6 bp using the second model.

Stochastic models were built in the way described above in order to distinguish between coding and non-coding DNA sequences. The models demonstrated substantial species independence, although more specific species dependent models may provide greater accuracy. The experiments concerned the construction of a coding model and a non-coding model each using 200 DNA strings divided into test sets and validation sets respectively.

Non-homogeneous trees that were applied to DNA segments of length 162 bp and a zero threshold yielded a 94.8 percent of correct rejections (True negative) and 93 percent of correct acceptance (True Positive). Using another model with different threshold, we obtained a 99.5% of correct rejections for the coding model and a 21% of false rejections. Using the same model for the non-coding model, the percentage of correct rejections was 100% and the percentage of false rejections was 12%.

It was noted that the coding model had a much smaller context tree than the non-coding model.

Other DNA applications include the ability to distinguish, analyze and classify: i) exons and introns; ii) Splice Sites; iii) Terminators; vi) Poly A; v) Proteins; vi) other biological sequences that share functionality features. There is also provided the possibility of predicting the structure of a protein.

Medical applications for the above embodiments are numerous. Any signal representing a body function can be discretized to provide a finite set of symbols. The symbols appear in sequences which can be modeled and changes in the sequence can be indicated by the comparison step referred to above. Thus, medical personnel are provided with a system that can monitor a selected bodily function and which is able to provide an alert only when a change occurs. The method is believed to be more sensitive than existing monitoring methods.

A further application of the modeling and comparison process is image processing and comparison. A stochastic model of the kind described above can be built to describe an image, for example a medical image. The stochastic model may then be used to compare other images in the same way that it compares other data sequences. Such a system is useful in automatic screening of medical image data to identify features of interest. The system can be used to compare images of the same patient taken at different times, for example to monitor progress of a tumor. Alternatively, it could be used to compare images taken from various patients already diagnosed with a given condition, against an image showing the same view of a patient being tested.

A further application of the modeling and comparison process is in pharmaceutical research. A protein (e.g., an enzyme, receptor, ligand, etc.) carrying out a particular function is required. A series of proteins which all carry out the required function are sequenced or have a known sequence and a model derived from all the sequences together may define the required sequence for the desired protein. At a higher level of organization, a protein (e.g., an enzyme, receptor, ligand, etc.) carrying out a particular function is required. A series of proteins which all carry out the required function are structurally analyzed or have a known structural analysis (obtained, for example, by X-ray cristalography) and a model derived from all the sequences together may define the required structure for the desired protein.

A further application of the modeling and comparison process is to analyze nucleic acid microarrays, such as DNA chips, to determine, for example the nature (e.g., the base sequence) of the materials to which they have been exposed (e.g., nucleic acids of unknown or undetermined sequence).

A further application of the modeling and comparison process is to analyze protein (e.g., antigens or antibodies) microarrays, such as protein chips, to determine, for example the nature of the materials to which they have been exposed (e.g., antibodies or antigens, respectively).

A further application of the modeling and comparison process as described above is in forecasting. For example, such forecast can be applied to natural data—such as weather conditions, or to financial related data sucha s stock markets. As the model expresses a statistical distribution of the sequence, it is able to give a probability forecast for a next expected symbol given a particular received sequence. A further application of the present embodiments is to sequences of multi-input single output data, such as records in a database, which may for example represent different features of a given symbol. Considering a database with records that arrive at consecutive times, the algorithm, (when extended to multi-dimensions), may compare a sequence of records and decide whether they have similar statistical properties to the previous records in the database. The comparison can be used to detect changes in the characteristics of the source which generates the records in the database.

Likewise the database may already be in place, in which case the algorithm may compare records at different locations in the database.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

The invention claimed is:

1. An apparatus for determining statistical consistency in spatially related data, wherein said spatially related data is expressible in terms of a finite set of symbols, the apparatus comprising:
a sequence input configured for receiving a spatially related data sequence of symbols selected from said finite set;
a modeler configured for producing at least one context tree model from at least part of said data sequence, wherein said context tree model comprises a set of conditional probabilities of symbols in said sequence,
a comparator configured for calculating a statistical distance between said context tree model and a reference model, and for comparing said calculated statistical distance to a user-defined level so as to determine if said context tree model and said reference model are statistically consistent; and
an output interface configured for outputting said determination to a display, to a user, in a graphical format, or in a user readable format, thereby allowing monitoring of said spatially related data.

2. The apparatus according to claim 1, wherein said modeler comprises:
a tree builder for expressing said symbols as a series of counters within nodes in said context tree model, each node having a counter for each symbol, each node having a position within said context tree model, said position expressing a symbol sequence and each counter indicating a number of its corresponding symbol which follows a symbol sequence of its respective node, and
a tree reducer for reducing said context tree model to an irreducible set of conditional probabilities of relationships between symbols in said input data sequence.

3. The apparatus according to claim 1, said reference model being a model constructed using another part of said input spatially related data sequence.

4. The apparatus according to claim 1, said comparator comprising a statistical processor for determining a statistical distance between said context tree model and said reference model.

5. The apparatus according to claim 1, wherein said comparator comprises a statistical processor for determining a difference in statistical likelihood between said context tree model and said reference model.

6. The apparatus according to claim 1, said statistical distance being a relative complexity measure.

7. The apparatus according to claim 4, wherein said statistical distance comprises an SPRT statistic.

8. The apparatus according to claim 4, wherein said statistical distance comprises an MDL statistic.

9. The apparatus according to claim 4, wherein said statistical distance comprises a Multinomial goodness of fit statistic.

10. The apparatus according to claim 4, wherein said statistical distance comprises a Weinberger Statistic.

11. The apparatus according to claim 4, wherein said statistical distance comprises a KL statistic.

12. The apparatus according to claim 2, said tree reducer comprising a tree pruner for removing from said tree any node whose counter values are within a threshold distance of counter values of a preceding node in said tree.

13. The apparatus according to claim 12, wherein said threshold distance is user selectable.

14. The apparatus of claim 13, wherein user selectable parameters further comprise a tree maximum depth.

15. The apparatus of claim 13, wherein user selectable parameters further comprise an algorithm buffer size.

16. The apparatus of claim 13, wherein user selectable parameters further comprise a value of at least one pruning constant.

17. The apparatus of claim 13, wherein user selectable parameters further comprise a length of input sequences.

18. The apparatus of claim 13, wherein user selectable parameters further comprise an order of input symbols.

19. The apparatus according to claim 12, wherein said tree reducer further comprises a path remover operable to remove any path within said tree that is a subset of another path within said tree.

20. The apparatus according to claim 1, wherein said data comprises a nucleic acid sequence.

21. The apparatus according to claim 1, wherein said data comprises an amino-acid sequence.

22. The apparatus according to claim 1, wherein said sequential data is an output of a medical sensor sensing bodily functions.

23. The apparatus according to claim 20, wherein said nucleic acid sequence is a promoter sequence and another nucleic acid sequence is a non-promoter sequence, wherein said stochastic modeler is operable to build models of said promoter sequence and said non-promoter sequence and said comparator is operable to compare a third nucleic acid sequence with each of said models to determine whether said third sequence is a promoter sequence or a non-promoter sequence.

24. The apparatus according to claim 20, wherein said nucleic acid sequence is a coding sequence and another nucleic acid sequence is a non-coding sequence, wherein said stochastic modeler is operable to build models of said coding sequence and said non-coding sequence and said comparator is operable to compare a third nucleic acid sequence with each of said models to determine whether said third sequence is a coding sequence or a non-coding sequence.

25. The apparatus according to claim 20, wherein said nucleic acid sequence is a repetitive sequence and another nucleic acid sequence is a non-repetitive sequence, wherein said stochastic modeler is operable to build models of said repetitive sequence and said non-repetitive sequence and said comparator is operable to compare a third nucleic acid sequence with each of said models to determine whether said third sequence is a repetitive sequence or a non-repetitive sequence.

26. The apparatus according to claim 20, wherein said nucleic acid sequence is a non-coding sequence and another nucleic acid sequence is a non-non-coding sequence, wherein said stochastic modeler is operable to build models of said non-coding sequence and said non-non-coding sequence and said comparator is operable to compare a third nucleic acid sequence with each of said models to determine whether said third sequence is a non-coding sequence or a non-non-coding sequence.

27. The apparatus according to claim 4, wherein said data sequence comprises image data of a first image.

28. The apparatus according to claim 27, said distance being indicative of a statistical distribution within said image.

29. The apparatus according to claim 28, further comprising an image comparator for comparing said statistical distribution with a statistical distribution of another image.

30. The apparatus according to claim 29, said other image being of a same view as said first image taken at a different time, said distance being indicative of time dependent change.

31. The apparatus according to claim 27, said image data comprising medical imaging data, said statistical distance being indicative of deviations of said data from an expected norm.

32. The apparatus according to claim 1, applicable to a database to perform data mining on said database.

33. The apparatus according to claim 1, said stochastic model being constructed from descriptions of a plurality of enzymes for carrying out a given task, said model thereby providing a generic structural description of an enzyme for carrying out said task.

34. The apparatus according to claim 1, said model being usable to analyze results of a nucleic acid micro array.

35. The apparatus according to claim 1, said model being usable to analyze results of a protein microarray.

36. An apparatus for distinguishing between data sequences of a first kind and data sequences of a second kind, each kind being expressible in terms of a same finite set of symbols, the apparatus comprising:
- a first sequence input and modeler unit configured for obtaining a set of data sequences of said first kind and building a first context tree model thereof,
- a second sequence input and modeler unit configured for obtaining a set of data sequences of said second kind and building a second context tree model thereof,
- a sequence input and comparison unit configured for taking a further data sequence and comparing it with each of said first and second context tree models;
- the sequence input and comparison unit further configured for determining whether said further data sequence belongs to one of said first and second context tree models; and
- an output unit associated with said sequence input and comparison unit and configured for outputting said determination to a display, to a user, in a graphical format, or in a user readable format thereby allowing monitoring of spatially related data.

37. The apparatus of claim 36, wherein said biological sequences are amino acid sequences.

38. The apparatus of claim 36, wherein the sequences of said first kind are nucleic acid promoter sequences.

39. The apparatus of claim 36, wherein the sequences of said first kind are nucleic acid coding sequences and the sequences of said second kind are nucleic acid non-encoding sequences.

40. The apparatus of claim 39, wherein the sequences are non-species specific, thereby constructing models which are non-species specific.

41. The apparatus of claim 36, wherein the data sequences are biological sequences.

42. The apparatus of claim 36, wherein the data sequences comprises image data of a first image.

43. The apparatus of claim 41, wherein said biological sequences are amino acid sequences.

44. The apparatus according to claim 1, wherein said input spatially related data is representative of one of an image, a molecule and a microarray.

45. The apparatus according to claim 36, applicable to a database to perform data mining on said database.

* * * * *